(12) United States Patent
Liu et al.

(10) Patent No.: US 7,993,271 B2
(45) Date of Patent: Aug. 9, 2011

(54) SYSTEM AND METHOD FOR SCREENING TISSUE

(75) Inventors: Jun Liu, Columbus, OH (US); Mauro Ferrari, Dublin, OH (US); Stanislav I. Rokhlin, Columbus, OH (US); Daniel D. Sedmak, Columbus, OH (US)

(73) Assignee: The Ohio State University, Columbus, OH (US)

( * ) Notice: Subject to any disclaimer, the term of this patent is extended or adjusted under 35 U.S.C. 154(b) by 1079 days.

(21) Appl. No.: 11/750,161

(22) Filed: May 17, 2007

(65) Prior Publication Data

US 2007/0299340 A1    Dec. 27, 2007

Related U.S. Application Data

(63) Continuation of application No. 10/251,309, filed on Sep. 20, 2002, now abandoned.

(51) Int. Cl.
*A61B 8/00* (2006.01)

(52) U.S. Cl. .......... 600/437; 600/442; 600/446

(58) Field of Classification Search ........ 600/407, 600/408, 437–461; 601/2–4; 604/19–22
See application file for complete search history.

(56) References Cited

U.S. PATENT DOCUMENTS

| | | | |
|---|---|---|---|
| 4,858,124 A * | 8/1989 | Lizzi et al. ............ 600/443 |
| 4,882,315 A | 11/1989 | Chiodini et al. | |
| 4,895,836 A | 1/1990 | Chiodini et al. | |
| 4,920,099 A | 4/1990 | Chiodini et al. | |
| 4,981,554 A | 1/1991 | Loconsolo et al. | |
| 5,135,000 A * | 8/1992 | Akselrod et al. ............ 600/458 |
| 5,178,147 A * | 1/1993 | Ophir et al. ............ 600/437 |
| 5,293,870 A * | 3/1994 | Ophir et al. ............ 600/437 |
| 5,432,169 A | 7/1995 | Quadri et al. | |
| 5,478,817 A | 12/1995 | Melloni et al. | |
| 5,593,982 A | 1/1997 | Quadri et al. | |
| 5,606,971 A * | 3/1997 | Sarvazyan ............ 600/438 |
| 5,651,900 A | 7/1997 | Keller et al. | |
| 5,728,164 A | 3/1998 | Ferrari et al. | |
| 5,731,345 A | 3/1998 | Gobbini et al. | |
| 5,770,076 A | 6/1998 | Chu et al. | |
| 5,798,042 A | 8/1998 | Chu et al. | |
| 5,893,974 A | 4/1999 | Keller et al. | |
| 5,938,923 A | 8/1999 | Tu et al. | |
| 5,948,255 A | 9/1999 | Keller et al. | |
| 5,955,632 A | 9/1999 | Gobbini et al. | |
| 5,985,164 A | 11/1999 | Chu et al. | |
| 5,985,328 A | 11/1999 | Chu et al. | |
| 6,015,599 A | 1/2000 | Keller et al. | |
| 6,044,981 A | 4/2000 | Chu et al. | |
| 6,107,102 A | 8/2000 | Ferrari | |

(Continued)

OTHER PUBLICATIONS

Eye on the Future: Nanotechnology: The Engineered Course of Treatment, Use of nanoscale devices is helping to revolutionize medical treatment and research. By Mauro Ferrari and Jun Liu, Mechanical Engineering, Dec. 2001.

(Continued)

*Primary Examiner* — Sanjay Cattungal

(74) *Attorney, Agent, or Firm* — Calfee, Halter & Griswold LLP

(57) ABSTRACT

A system and method for screening tissue is provided. The system provides a computer-based system for distinguishing between normal and potentially abnormal tissue. The system includes computer components for generating and receiving ultrasonic waves, for storing a tissue model, and for analyzing received ultrasonic waves in the context of the tissue model.

23 Claims, 20 Drawing Sheets

U.S. PATENT DOCUMENTS

| | | | |
|---|---|---|---|
| 6,355,270 | B1 | 3/2002 | Ferrari et al. |
| 6,405,066 | B1 | 6/2002 | Essenpreis et al. |
| 6,494,840 | B1 * | 12/2002 | Mak et al. ............. 600/446 |
| 6,508,768 | B1 * | 1/2003 | Hall et al. ............. 600/443 |
| 6,530,944 | B2 * | 3/2003 | West et al. ............. 607/88 |
| 6,558,324 | B1 * | 5/2003 | Von Behren et al. ...... 600/440 |
| 6,610,011 | B2 | 8/2003 | Emery |
| 6,618,620 | B1 | 9/2003 | Freundlich et al. |
| 6,645,148 | B2 | 11/2003 | Nguyen-Dinh et al. |
| 6,875,176 | B2 * | 4/2005 | Mourad et al. .......... 600/442 |
| 6,941,231 | B2 * | 9/2005 | Zeroug et al. ........... 702/39 |
| 7,014,839 | B2 | 3/2006 | Klaveness et al. |
| 7,022,077 | B2 * | 4/2006 | Mourad et al. .......... 600/449 |
| 7,815,574 | B2 * | 10/2010 | Mourad et al. .......... 600/453 |
| 2003/0023168 | A1 | 1/2003 | Benjamin |
| 2003/0161513 | A1 * | 8/2003 | Drukker et al. ......... 382/128 |
| 2004/0059220 | A1 * | 3/2004 | Mourad et al. .......... 600/442 |
| 2005/0113697 | A1 | 5/2005 | Ottoboni et al. |
| 2006/0079773 | A1 | 4/2006 | Mourad et al. |
| 2007/0016031 | A1 * | 1/2007 | Mourad et al. .......... 600/437 |
| 2009/0076732 | A1 * | 3/2009 | Sprigle et al. ........... 702/19 |
| 2009/0240150 | A1 * | 9/2009 | Wang et al. ............. 600/443 |

OTHER PUBLICATIONS

A Discrete Model for the High Frequency Elastic Wave Examination on Biological Tissue. By Jun Liu and Mauro Ferrari. Computer Modeling in Engineering Sciences, vol. 4, No. 3&4, pp. 421-430, Tech Science Press, 2003.

Mechanical spectral signatures of malignant disease? A small-sample, comparative study of continuum vs. nano-biomechanical data analyses. By Jun Liu and Mauro Ferrari. Disease Markers, vol. 18 (4), pp. 175-183, IOS Press, 2002.

Advances in Doublet Mechanics. By Mauro Ferrari, Vladimir T. Granik, Ali Imam and Joseph C. Nadeau. Springer-Verlag, Physics Editorial Department II, Tiergartenstrasse 17, D-69121, Heidelberg, Germany, 1997 (Chapters 1, 5 and 6).

A Nanomechanical Approach For Ultrasonic Tissue Analysis, Dissertation. By Jun Liu, M.S. UMI Microform Number 3072916, ProQuest Information and Learning Company, 2003.

* cited by examiner

SYSTEM AND METHOD FOR SCREENING TISSUE

This application is a continuation of U.S. application Ser. No. 10/251,309, filed Sep. 20, 2002, which is hereby incorporated by reference.

TECHNICAL FIELD

The methods, systems, and computer readable media described herein relate generally to screening tissue and more particularly to analyzing ultrasonic waves interacting with tissue, where the analysis relies on a biomechanical response model derived from a quantitative correlation of tissue responses to ultrasonic interrogation.

BACKGROUND

Technologies employed for early detection of diseased tissue (e.g., cancer) include visual inspection, x-ray computer tomography, ultrasound, positron emission tomography (PET) scanning, magnetic resonance imaging (MRI) and so on. While such technologies have had various degrees of success detecting disease in an early stage, improvements are constantly being sought. Definitive diagnosis, especially of malignant disease, still typically includes biopsy, an invasive, costly, time-consuming procedure.

It is possible to obtain quantitative information on the physical characteristics of a material through ultrasound inspection. Non-destructive ultrasonic testing has been employed for evaluating engineering structures by the determination of their relevant material properties. Translating this approach to biomedical applications (e.g., disease screening) is complicated due to the lack of appropriate theoretical models that facilitate reconstructing physical properties of biological tissue. In particular, models derived from the conventional mechanics of solids, including biological domains, are based on a continuum representation. The continuum representation postulates the existence of a typical dimension or Representative Volume Element (RVE), below which matter may be assumed to be continuous and fully homogeneous. On these foundations, mechanical phenomena may then be represented in a differential equation format. This modeling strategy breaks down when it is not possible to establish a continuum RVE. Establishing a continuum RVE is not possible when phenomena are examined on a length scale at which the discrete, inhomogeneous nature of the media is evident, as frequently encountered in biological tissue examination.

Approaches have been developed that attempt to address these concerns by representing complex composite domains as continua with continuum inclusions. These theories, collectively known as "micromechanics", still suffer from the limitation that they do not incorporate the discrete nature of matter, while remaining computationally manageable at domain sizes that are currently incomparable to lattice dynamics, ab-initio approaches, or molecular dynamics.

Additionally, measuring mechanical properties of biological soft tissue has been elusive because tissue is not well-behaved material. Indeed, mechanically soft tissue is known as being inhomogeneous, anisotropic, non-linear, and viscoelastic.

SUMMARY

The following presents a simplified summary of methods, systems, and computer readable media for screening tissue by ultrasonic waves to facilitate providing a basic understanding of these items. This summary is not an extensive overview and is not intended to identify key or critical elements of the methods, systems, and computer readable media or to delineate the scope of these items. This summary provides a conceptual introduction in a simplified form as a prelude to the more detailed description that is presented later.

Early detection of diseased tissue (e.g. cancer) can benefit patients, physicians, providers, and others. Thus, there have been efforts to identify and quantify, for example, cancer "signatures" toward this purpose. One type of signature relates to the physical properties of the diseased tissue as compared to normal counterparts. Such signatures are identifiable in part because of the well-recognized phenomenon that changes in tissue physical properties are associated with disease inception. Example physical properties include, but are not limited to, tissue elasticity (e.g., stiffness, hardness), cellular geometry (e.g., cell size, cell shape), internodal distance, particle size, tissue micro-architecture (e.g., spatial distribution of cells and cellular matrices), and so on.

One way to mechanically test tissue so that the effects of the physical properties can be measured is to direct high frequency ultrasonic waves at the tissue. These waves interact with (e.g., reflect from and/or transmit through) the tissue, and the reflected and/or transmitted waves can then be analyzed to estimate the physical properties of tissue through its mechanical response to sound waves. The quantitative information thus obtained offers beneficial implications for separating normal tissue from abnormal tissue.

Thus, in one aspect, the application describes a tissue screening system. The system includes an ultrasonic wave producer that produces ultrasonic waves that are directed at a tissue to be screened. The waves interact with the tissue and produce a set of resulting ultrasonic waves. The system also includes an ultrasonic wave receiver that receives resulting ultrasonic waves and an analyzer operably connected to the ultrasonic wave producer and/or the ultrasonic wave receiver. In one example, reflected ultrasonic pulses are transformed to frequency domain through Fast Fourier Transformation (FFT) and become reflection spectra. The analyzer differentiates tissue regions by analyzing parameters (e.g., reflection spectra) of the resulting ultrasonic waves. In another example, the system also includes a tissue mechanical properties model in data communication with the analyzer. The model stores information associated with quantitative correlations between the physical properties of inspected tissue and reflection spectra. In one example, the model stores information derived from previous measurements and studies on the reflection spectra and/or physical properties of normal and abnormal tissue. In another example, the model stores information associated with an inverse algorithm, which may be implemented in software, that facilitates reconstructing physical properties of inspected tissue. Thus, the analyzer utilizes information including, but not limited to, reflected spectra, and reconstructed physical properties, to distinguish between normal tissue and malignant tissue.

In another aspect, the application describes a method for screening tissue. In one example the method includes directing an ultrasonic wave at a tissue to be screened, receiving second ultrasonic waves produced by the first ultrasonic wave interacting with the tissue to be screened, and determining whether an area of the tissue to be screened should be tagged. The determining may include, for example, analyzing one or more parameters associated with the second ultrasonic waves in the context of a tissue mechanical properties model. In one example, the tissue may first be treated with a nanoparticle contrast agent to facilitate identifying and differentiating tissue areas.

While this summary describes in general the propagation and analysis of high frequency elastic waves, it is to be expected that one skilled in the art will have an understanding of such waves, and thus further discussion is limited herein for the sake of brevity. A discussion of reflection coefficients of tissue is included in "A Discrete Model For The High Frequency Elastic Wave Examination On Biological Tissue", which is incorporated herein by reference as the type of material with which one skilled in the art would be familiar. Similarly, while this summary describes in general the theory of nanomechanics, it is to be expected that one skilled in the art will have an understanding of nanomechanics. A discussion of nanomechanics can be found in "Advances in Doublet Mechanics", Ferrari et. al, ISBN 3-540-62061-3, Springer 1997, which is incorporated herein by reference as the type of material with which one skilled in the art would be familiar.

Certain illustrative example methods, systems, and computer readable media are described herein in connection with the following description and the annexed drawings. These examples are indicative, however, of but a few of the various ways in which the principles of the methods, systems, and computer readable media may be employed and thus are intended to be inclusive of equivalents. Other advantages and novel features may become apparent from the following detailed description when considered in conjunction with the drawings.

DETAILED DESCRIPTION

Figure 1:
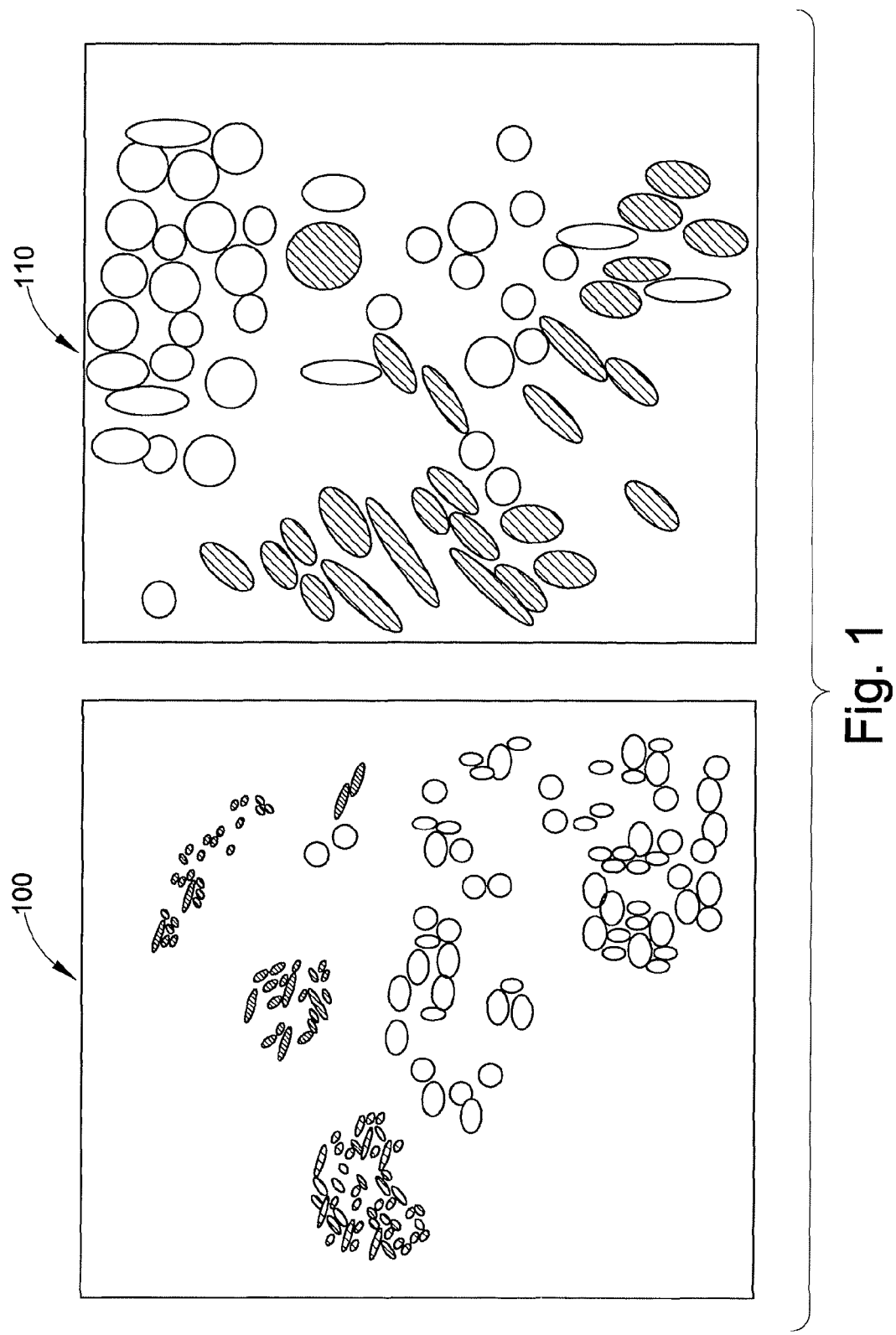
FIG. 1 illustrates two simulated tissue samples, one of normal tissue, and one of tissue affected by cancer (e.g., invasive ductal carcinoma).

Example methods, systems, and computer media are now described with reference to the drawings, where like reference numerals are used to refer to like elements throughout. In the following description, for purposes of explanation, numerous specific details are set forth in order to facilitate thoroughly understanding the methods, systems and computer readable media. It may be evident, however, that the methods, systems, and computer readable media can be practiced without these specific details. In other instances, well-known structures and devices are shown in block diagram form in order to simplify description.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program, and a computer. By way of illustration, both an application running on a server and the server can be computer components. One or more computer components can reside within a process and/or thread of execution and a computer component can be localized on one computer and/or distributed between two or more computers.

"Logic", as used herein, includes but is not limited to hardware, firmware, software, and/or combinations of each to perform a function(s) or an action(s). For example, based on a desired application or needs, logic may include a software controlled microprocessor, discrete logic such as an application specific integrated circuit (ASIC), or other programmed logic device. Logic may also be fully embodied as software.

An operable connection is one in which signals and/or actual communication flow and/or logical communication flow may be sent and/or received. Usually, an operable connection includes a physical interface, an electrical interface, and/or a data interface, but it is to be noted that an operable connection may consist of differing combinations of these or other types of connections sufficient to allow operable control.

"Signal", as used herein, includes but is not limited to one or more electrical or optical signals, analog or digital, one or more computer instructions, a bit or bit stream, or the like.

"Software", as used herein, includes but is not limited to, one or more computer readable and/or executable instructions that cause a computer or other electronic device to perform functions, actions and/or behave in a desired manner. The instructions may be embodied in various forms like routines, algorithms, modules, methods, threads, and/or programs. Software may also be implemented in a variety of executable and/or loadable forms including, but not limited to, a stand-alone program, a function call (local and/or remote), a servelet, an applet, instructions stored in a memory, part of an operating system or browser, and the like. It is to be appreciated that the computer readable and/or executable instructions can be located in one computer component and/or distributed between two or more communicating, co-operating, and/or parallel processing computer components and thus can be loaded and/or executed in serial, parallel, massively parallel and other manners.

Biological tissue is usually granular or cellular by nature. The onset of disease (e.g., cancer) may cause changes in tissue microstructures. For example, in Figure One, two simulated slides that compare normal tissue with diseased tissue are illustrated. The two tissues may have differences in properties including but not limited to, micromoduli, internodal distance, and/or particle size. Micromoduli and internodal distance are physical parameters of matter at its granular or node level, possibly down to the nanoscale. Micromoduli refers to the constants that appear in the constitutive relationships between the microstresses and the microstrains. Internodal distance refers to the distance between two granules or nodes that have effective mechanical interaction. In one example, internodal distance can be equivalent to particle size if the matter is composed of space-filling granular components.

The types of tissue that can be examined by the systems and methods described herein include, but are not limited to, external surface tissue (e.g., skin surface), and internal surface tissue (e.g., stomach lining). The varied physical properties impact mechanical responses like reflectivity and transmissivity of tissue, which facilitates identifying pathologically interesting tissue areas.

Two example mechanical parameters of tissue—micromoduli and particle size—can be analyzed to facilitate screening for diseased/altered tissue. Particle size and/or internodal distance is relevant, for example, to cell size. Referring again to FIG. 1, sample 100 simulates healthy tissue, which may exhibit a first set of responses to mechanical waves due to a first set of mechanical properties. While healthy tissues may exhibit a range of responses to ultrasonic waves, various measurable parameters (e.g., reflection coefficients) and physical properties for healthy tissues can be experimentally measured and theoretically solved for using various mathematical and engineering techniques described and/or referred to herein. Sample 110 simulates unhealthy tissue that has been affected by cancer (e.g., invasive ductal carcinoma). Sample 110 will, therefore, likely exhibit a second set of responses to mechanical waves due to a second set of mechanical properties. Again, while unhealthy tissues may exhibit a range of responses to ultrasonic waves, various measurable parameters (e.g., reflection coefficients) and physical properties for unhealthy tissues can be experimentally measured and theoretically solved for using various mathematical and engineering techniques described and/or referred to herein. With parameters like reflection coefficients experimentally measured and theoretically solved for, systems and methods can employ a tissue mechanical properties model based on the measured and solved for parameters (e.g., reflection coefficients) to facilitate screening tissue for areas that are (un)healthy.

Developing a model based on the reflection coefficients and/or other measurable parameters required studying physical properties (e.g., micromoduli, particle size) of tissue in an experimental setting. To facilitate characterizing mechanical properties of healthy and unhealthy tissues and/or the mechanical responses of tissues to ultrasonic waves, experiments were conducted that measured, among other things, relationships discovered by analyzing, for example, the reflected waves, and the spectra created by such waves after interacting with tissue samples. Mechanical properties of tissue can be analyzed by examining, for example, the stresses and strains in a tissue sample as revealed by the relationships between incident and reflected waves. Both continuum mechanics and nanomechanics can be employed to study the mechanical properties and responses of tissue, from which theoretical models of such properties and responses can be constructed.

Mechanical waves cause displacements of particles in a sample to be studied. Nanomechanics is distinguishable from micromechanics and continuum mechanics based on its multi-scale nature and its ability to model discrete nodes at finite distances as small as the nanometer range. Thus, models can be built for analyzing and characterizing plane elastic wave propagation in tissue. To construct the theoretical models, displacements were assumed to be in the forms:

$$u^{(i)} = A_i \exp(ik_i(x_1 \sin\theta_i - x_2 \cos\theta_i - c_i t))$$

where $u^{(i)}$ is the displacement of the ith wave, $A_i$ is the amplitude of the displacement, $k_i$ is the wave number, $\theta_i$ is the propagation angle with respect to the perpendicular direction, and $c_i$ is the wave speed. These forms of the displacements satisfy equilibrium conditions in both continuum and nanomechanical models. Thus, the displacements represent a complete solution under appropriate boundary and/or continuity conditions.

Nanomechanics provides a framework for studying the node level microstresses and microstrains, as revealed by relationships between incident and reflected waves, that facilitates solving for the reflection coefficients and for building a model that facilitates real-time tissue screening. Under the theoretical framework of nanomechanics, physical domains are composed of discrete entities or nodes that are geometrical points relating to each other through finite distances and specific orientations. In a linear elastic context, node-level properties relating axial stress and strain can be characterized by:

$$p_\alpha = \sum_\beta A_{\alpha\beta} \varepsilon_\beta$$

where $p_\alpha$ is the overall nodal stress in the $\alpha$-doublet, and $\epsilon_\beta$ is the axial nodal strain associated with $\beta$-doublet, and $A_{\alpha\beta}$ is the micromodulus between nodes $\alpha$ and $\beta$. Thus, $A_{\alpha\beta}$'s are the node-level counterparts of Lame's constants in continuum mechanics. The strain in the $\alpha$-doublet can be computed as follows:

$$\varepsilon_\alpha = \sum_{i,j=1}^{3} \tau_{\alpha i} \tau_{\alpha j} \frac{\partial u_i}{\partial x_j} + \frac{1}{2} \eta_\alpha \sum_{i,j,k=1}^{3} \tau_{\alpha i} \tau_{\alpha j} \tau_{\alpha k} \frac{\partial^2 u_i}{\partial x_j \partial x_k}$$

where $\epsilon_\alpha$ is the nodal strain associated with node $\alpha$, $\tau$'s are the direction cosines of the unit vectors connecting two nodes, $u_1$ is the displacement at $x_1$ direction, $u_2$ is the displacement at $x_2$ direction, and $\eta_\alpha$ is the internodal distance associated with node $\alpha$. $\eta_\alpha$ may be interpreted as the effective radius of penetration of the mechanical contact forcing along the $\alpha$ node direction.

Nanomechanics facilitates expressing macro (e.g., continuum) stresses in terms of micro stresses and architecture. This feature facilitates analyzing tissue microstructural characteristics based on information measured at the macro-level. One example transition relationship is:

$$\sigma_{ij} = \sum_{\alpha=1}^{n} \left( \tau_{\alpha i} \tau_{\alpha j} p_\alpha - \frac{\eta}{2} \tau_{\alpha i} \tau_{\alpha j} \tau_{\alpha k} \frac{\partial p_\alpha}{\partial x_k} \right)$$

where $\sigma_{ij}$ is the symmetric, second-rank continuum stress tensor.

The governing equation for elastic plane wave propagation also takes a different format compared to continuum mechanics. The non-scale (at scale one) wave equation presented here is essentially equivalent to the equation in continuum mechanics At scale two, the wave equations in nanomechanics are not equivalent to those in continuum mechanics. For example, the scale two equation incorporates the effect of the internodal distance $\eta$. It also has a fourth order differential term for the displacement with regard to spatial coordinates.

For scale 1, $$\sum_{\alpha=1}^{n} \sum_{\beta=1}^{n} A_{\alpha\beta} \tau_{\alpha i} \tau_{\alpha j} \tau_{\beta k} \tau_{\beta l} \frac{\partial^2 u_k}{\partial x_l \partial x_j} = \rho \frac{\partial^2 u_i}{\partial t^2}$$

For scale 2, $$\sum_{\alpha=1}^{n} \sum_{\beta=1}^{n} A_{\alpha\beta} \left[ \begin{array}{c} \tau_{\alpha i} \tau_{\alpha k_1} \tau_{\beta j} \tau_{\beta p_1} \frac{\partial^2 u_j}{\partial x_{k_1} \partial x_{p_1}} - \\ \frac{(\eta_\alpha)^2}{4} \tau_{\alpha i} \tau_{\alpha k_1} \tau_{\alpha k_2} \tau_{\beta j} \tau_{\beta p_1} \tau_{\beta p_2} \frac{\partial^4 u_j}{\partial x_{k_1} \partial x_{k_2} \partial x_{p_1} \partial x_{p_2}} \end{array} \right] =$$

$$\rho \frac{\partial^2 u_i}{\partial t^2}$$

In continuum mechanics, the retrievable properties are limited, by necessity, to macro elastic constants such as Young's modulus E, the shear modulus μ, and the corresponding attenuation coefficients. Thus, information about tissue scaling and micro-architecture is not provided through the continuum model. In the nanomechanical reconstruction, the node-level elastic constants $A_{\alpha\beta}$ (e.g., $A_{11}$ and $A_{44}$) and their attenuation counterparts are reconstructed along with parameters of the micro architecture (e.g., internodal distance $\eta$). In one example, the orientation of the nodes (the $\tau$'s) are defined to maintain a three dimensional isotropic arrangement at the macro level. However, it is to be appreciated that other orientations can be employed and/or reconstructed in accordance with aspects of the present invention.

Figure 4:
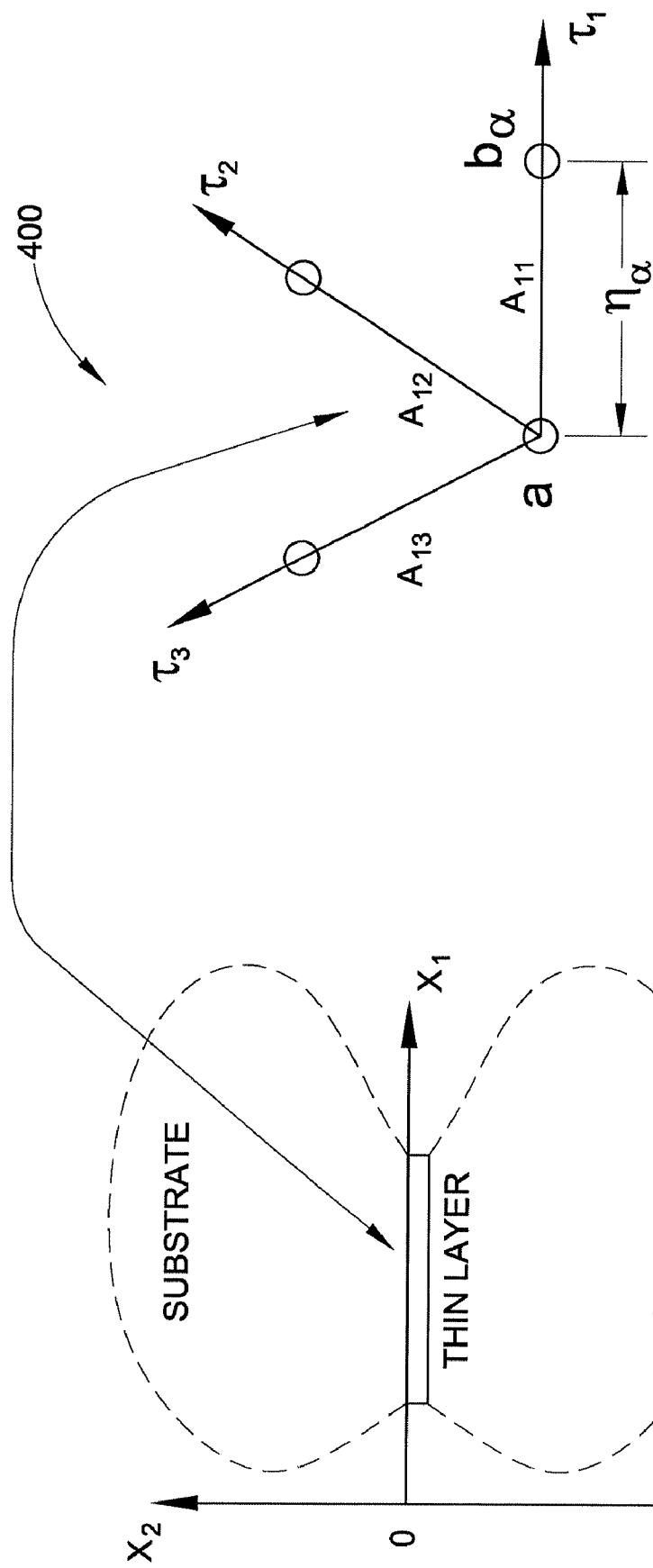
FIG. 4 is a schematic of a thin, discrete-structured (granular) layer embedded between two substrates modeled as isotropic elastic continua.

To facilitate solving for reflection coefficients and building a model, an elastic, discrete-structured (granular) layer sample of thickness d, was embedded between two infinite, isotropic, elastic domains with perfect bonding as in FIG. 4. In one experiment, thin tissue samples were embedded between glass plates and subjected to incident ultrasonic waves with known properties. The sample was then analyzed in an apparatus like that illustrated in FIG. 2.

Figure 2:
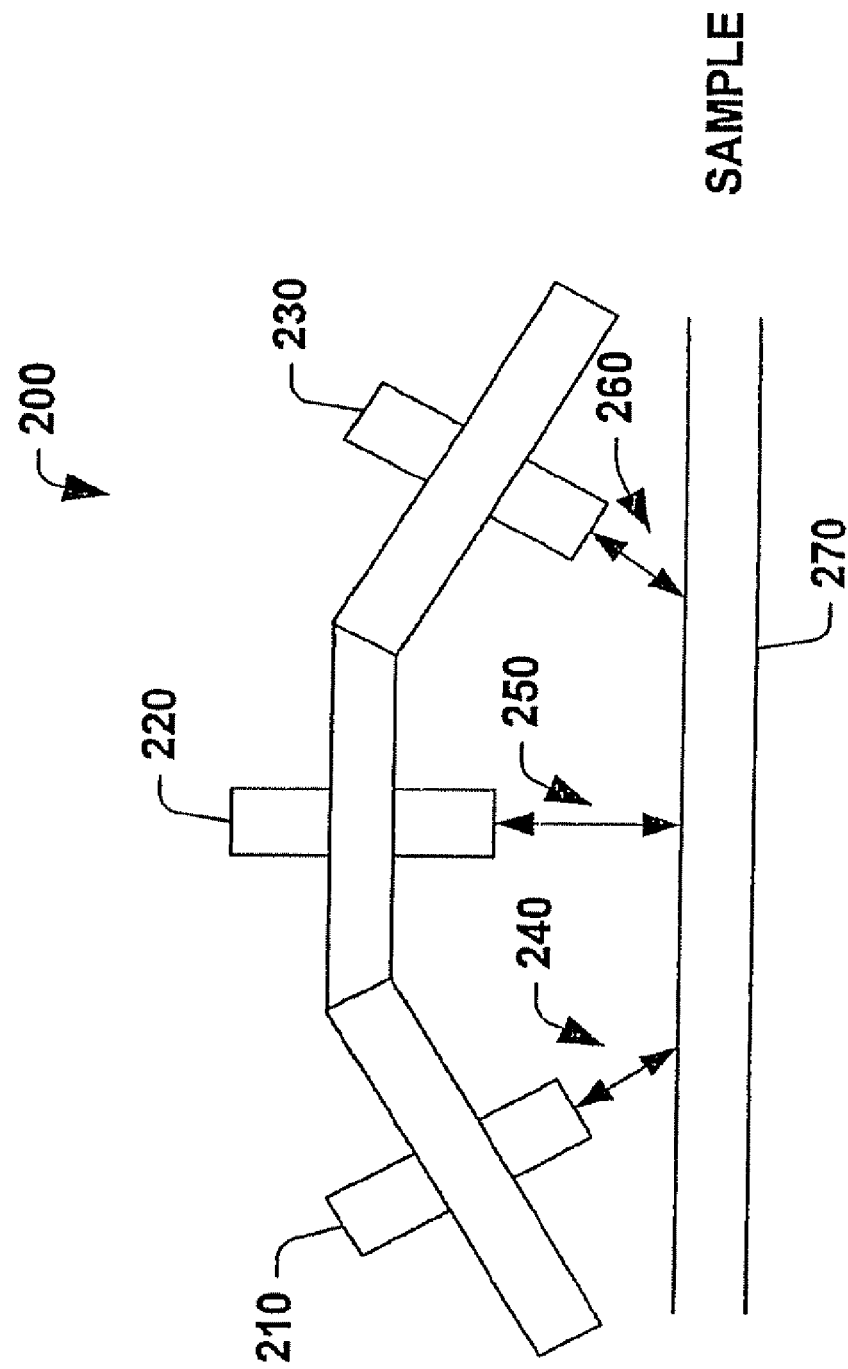
FIG. 2 illustrates an example experimental apparatus employed to analyze reflection coefficients.

Referring to FIG. 2, a first ultrasonic transmitter/receiver 210 may generate a first ultrasonic wave 240 (or set of waves) that is directed at a sample 270. The first wave(s) 240 will interact with (e.g., reflect, transmit) the sample 270 producing waves that can then be detected by, for example, the first transmitter/receiver 210 and/or other receivers (e.g., receivers 220, 230). Similarly, a second ultrasonic transmitter/receiver 220 may generate a second ultrasonic wave 250 (or set of waves) that interacts with the sample 270 and a third ultrasonic transmitter/receiver 230 may generate a third ultrasonic wave 260 (or set of waves) that interacts with the sample 270. In one example, 210 could be an ultrasonic transmitter only, 230 could be an ultrasonic receiver only, and 220 could act as both transmitter and receiver. While three transmitter/receivers are illustrated in apparatus 200, it is to be appreciated that a greater and/or lesser number of transmitter/receivers can be employed, and that other components (e.g., separate transmitters and receivers) can also be employed. Furthermore, waves generated by a first transmitter may be received by one or more receivers. In one example, the transmitter/receiver is a transducer, however, it is to be appreciated that other ultrasonic transmitters, receivers, and/or transmitter/receivers can be employed in accordance with aspects of the present invention. Additionally, while oblique and normal transmitters are illustrated, it is to be appreciated that the transmitters and/or receivers can be arranged in a variety of orientations (e.g., a ring of transducers, an array of transducers).

Figure 3:
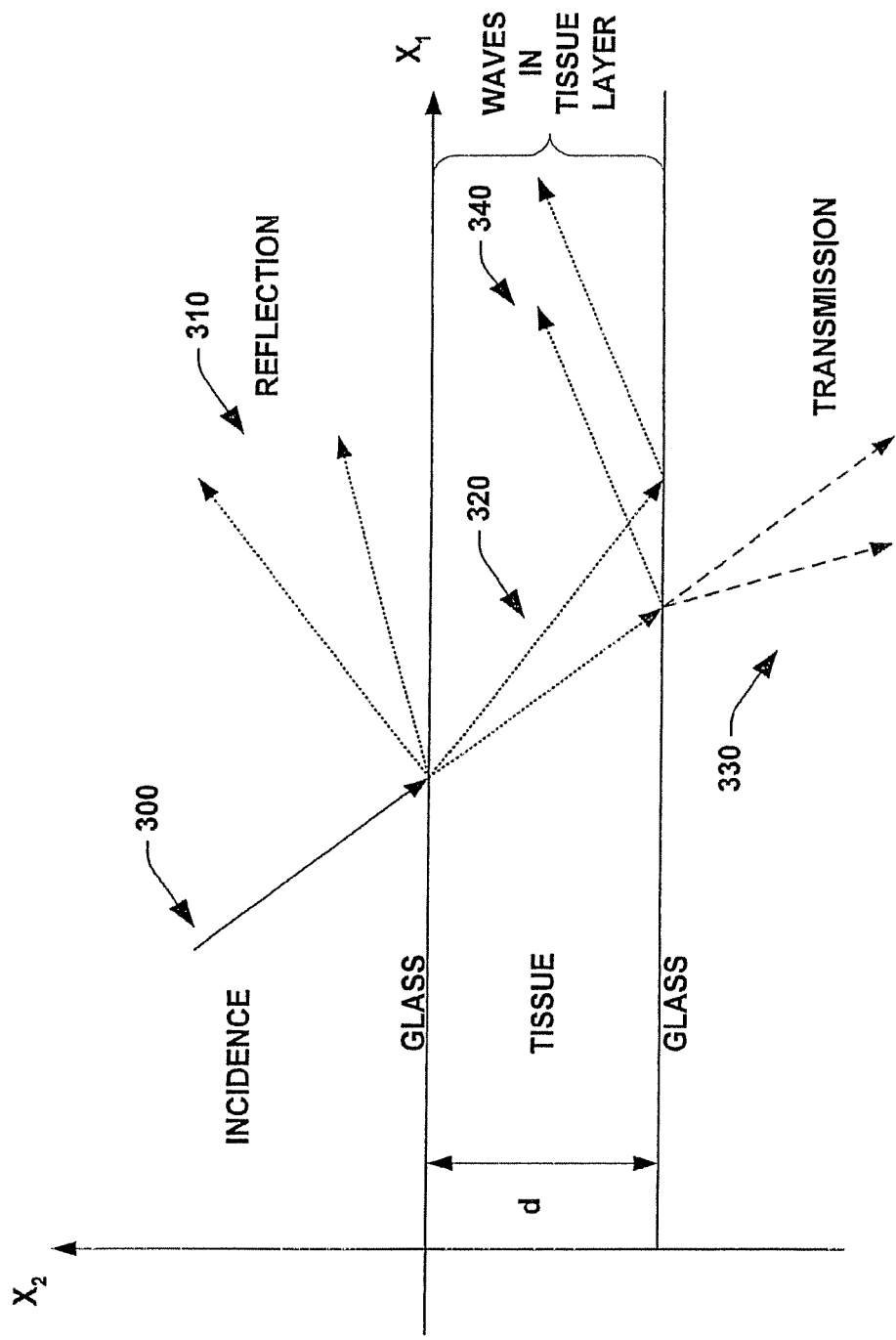
FIG. 3 illustrates an example incident wave and example waves that result from the interaction of the incident wave and a tissue sample.

Referring to FIG. 3, a time-harmonic plane wave 300 is directed at a tissue layer at an angle θ from the upper substrate to the structure. The incident wave 300 portions into reflections 310 and transmissions 320 when it hits the first material discontinuity (e.g., the upper interface between the thin layer and the substrate, for example, the glass). The transmitted waves 320 will further encounter the upper and lower interfaces (substrate/tissue, tissue/substrate) and cause formation of a series 340 of longitudinal and shear waves propagating up and down within the tissue. Multiple reflections at the top and bottom interfaces between tissue and substrates facilitate multiple waves with a phase lag to propagate within the thin layer. The constructive and destructive summations of these waves give rise to characteristic reflection spectra measurable within a range of frequencies.

As shown in FIG. 3, the reflected 310 and transmitted 330 waves propagate as longitudinal or shear waves with different angles and velocities. The angles of reflection and transmission at the interface are dictated by Snell's law, which holds that the ratio of the wave number and the sine of the propagation angle should remain constant at each interface. For example, at the upper interface, the following relationships hold:

$$\frac{k_0}{\sin\theta_0} = \frac{k_1}{\sin\theta_1} = \frac{k_2}{\sin\theta_2} = \frac{k_3}{\sin\theta_3} = \frac{k_4}{\sin\theta_4} = \frac{k_5}{\sin\theta_5} = \frac{k_6}{\sin\theta_6}$$

where $k_i$ is the wave number of the ith wave and $\theta_i$ is the propagation angle of the ith wave. Therefore, there is only one possible angle for each type of wave (longitudinal or shear) propagating in one direction (up or down).

If the displacement vector of the incident wave 300 is known (e.g., the amplitude and the incident angle are known), the eight other waves in the system can be uniquely determined assuming the material properties of the substrates and the layer are known. Furthermore, if the mechanical bonds between the substrate and the tissue are perfect, the following continuity conditions hold at each interface: continuity of the normal displacement; continuity of the normal stress; continuity of the shear displacement, and continuity of the shear stress. Imposing these conditions, a system of linear equations can be obtained, from which the unknown magnitudes of wave displacements $u^{(i)}$ can be obtained. The reflection/transmission coefficients, which are defined as the ratios of magnitudes of the reflection/transmission wave over the incident wave, can be computed according to:

$$R_S(f) = M_R(f)/M_I(f)$$

where $R_S(f)$ is the reflection/transmission coefficient at frequency f, $M_R(f)$ is the magnitude of the reflection/transmission at frequency f, and $M_I(f)$ is the magnitude of the incidence at frequency f. The reflection spectrum is generated by computing the reflection coefficients for multiple frequencies within a certain range, which is therefore a function of the set of physical properties of the tissue.

In the continuum mechanics model, both the layers of the substrates and the tissue were assumed to be isotropic and elastic continua. But in the nanomechanics model, the thin layer of tissue was represented as discrete nodes while the glass layers remained as continua for simplicity. A spatial arrangement (see FIGS. 4 and 5) of the nodes was chosen to yield a three dimensional isotropic medium at the macro scale. Within this micro architecture, each node relates to six other nodes at each octant. Micro level physical properties including, but not limited to, the internodal distance $\eta$, the orientation vector $\tau$ and the micro elastic constants $A_{11}$ and $A_{44}$ were specified for each pair of nodes ("doublets"). The reflection spectra in nanomechanics were thus obtained by specifying the micro level physical properties of the tissue layer.

The reflection coefficient for the layer can be defined as the magnitude of the ratio of the displacement of the reflected wave 310 from the layer over that of the incident wave 300. These equations facilitate analyzing the ratio:

$$R_L = \left|\frac{A_2}{A_0}\right|$$

$$R_S = \left|\frac{A_1}{A_0}\right|$$

where $R_L$ is the reflection coefficient of a reflected longitudinal wave, and $R_S$ is the reflection coefficient of a reflected shear wave. If the incident wave 300 is pulsed, (e.g., contains a range of frequency components), the reflection coefficients corresponding to that range of frequency generate a reflection spectrum. The reflection spectrum can then be analyzed, stored, and characterized, for example.

For the purpose of characterizing the mechanical properties of the thin layer with respect to its microstructural features, a discrete-structured layer, is illustrated in FIG. 4. The layer is identified by its density $\rho$, the micro elastic constants $A_{\alpha\beta}$, and internodal distances (or particle diameter) $\eta$. The substrates can be modeled with continuum elasticity, and the corresponding material properties are density $\rho$, and Lame's constants: $\lambda$ and $\mu$. The thin layer can thus be conceived of as comprising arrangements of nodes like arrangement 400.

In one example, the continuum properties of malignant and normal tissues did not differ in a statistically significant fashion (P>0.05). However, the same set of experimental measurements analyzed through the nanomechanical model yielded parameters that differed in a statistically significant manner (P<0.05) between adjacent normal and diseased tissue from the same person. Significant parameters included both node-level elastic constants $A_{11}$ and $A_{44}$, as well as the effective internodal distance $\eta$. Thus, a scanner being passed over a tissue area may detect a boundary between tissue with different mechanical characteristics, which facilitates identifying and/or tagging pathologically interesting tissue areas and/or locations.

Figure 5:
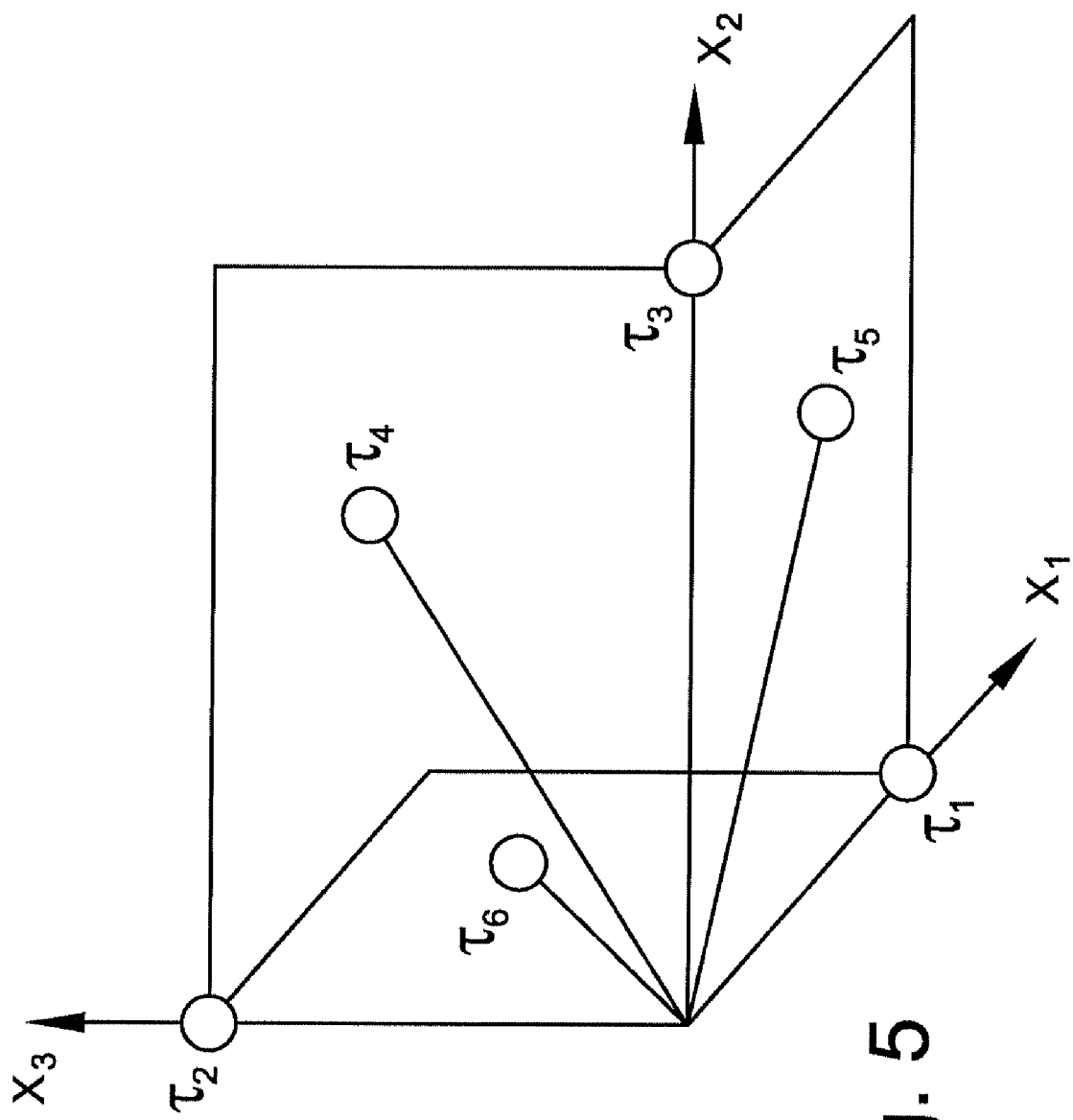
FIG. 5 illustrates an example nanomechanical microstructure representation.

FIG. 5 illustrates a particle arrangement as modeled by nanomechanics at a micro-structural level. Nanomechanics assumes material is composed of discrete nodes. The nodes are basically geometrical points in space. They are related to each other with a distance specified by $\eta$ and an orientation specified by vector $\tau$. The micro-level physical properties are governed by the micro moduli matrix $A_{\alpha\beta}$. Thus, FIG. 5 illustrates an arrangement of particles that facilitate characterizing axial constitutive relationships between micro-stress and micro-strain. Once the tissue has been characterized, an inverse algorithm can be applied to reconstruct quantitative information for parameters of the tissue properties. These parameters can include, but are not limited to, density, Young's modulus, and shear modulus for continuum model, and density, micro elastic constants, tissue micro-architecture and internodal distance, for nanomechanics. A least square minimization method can be employed to search for optimally estimated values on the parameters by solving:

$$\min_{x_i \in R^n} \frac{1}{2} \sum_{i=1}^{m} (|R_i^e| - |R_i^s|)^2$$

where $x_i$'s are the reconstructed parameters, n is the number of the parameters to be found, m is the number of data points at different frequencies, and $R^e$ and $R^s$ are the experimental reflection coefficients and simulated reflection coefficients, respectively.

Numerical analysis of the data acquired during the experiments illustrates that by using the nanomechanics model, statistically significant different mechanical responses can be measured between normal and diseased tissues. For example, the location of minima, the distance between minima, and the depth of the minima are different between normal and diseased tissue. Since different mechanical responses can be measured between normal and diseased tissue, ultrasonic waves can be employed to distinguish between such tissues.

Figure 6:
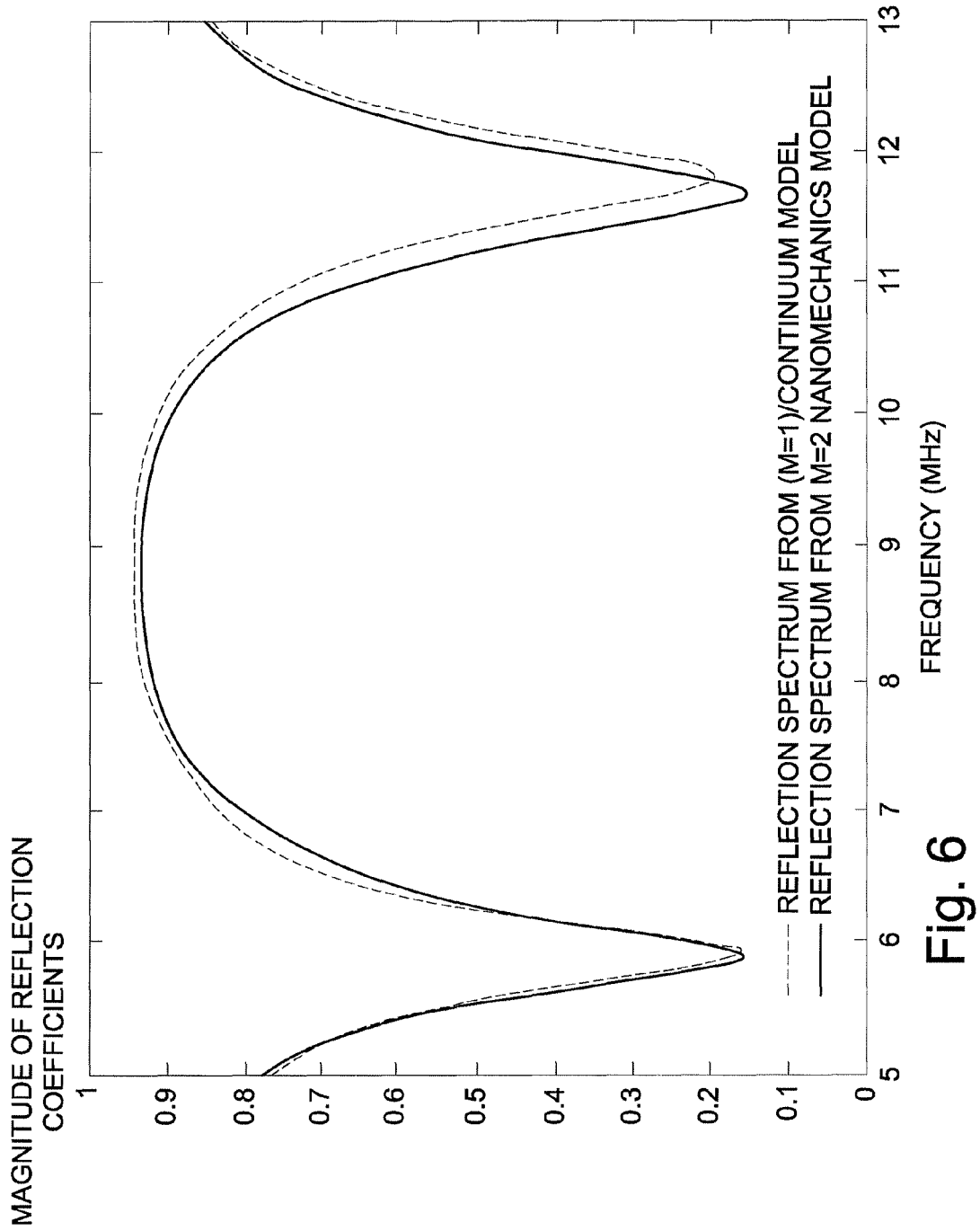
FIG. 6 illustrates reflection spectra from an example continuum model and an example nanomechanics model for "larger" internodal distances (e.g., $\eta=8$-$\mu m$).

Experiments employed to characterize non-continuum response features that may be significant to developing a discrete model for biological tissue can be carried out at various scales. In one example, characterization may be reached by limiting considerations to the approximation degree M=2. In one example, a simplified version of governing equations can be derived with the following assumption: that the particle interactions are longitudinal (central), so that the shear and torsional microstresses vanish everywhere. At different scales (e.g., M=1, M=2) the continuum model and nanomechanical models yield similar, yet appreciably differing results. As illustrated in FIG. 6, for a "large" internodal distance (e.g., $\eta$=8 $\mu$m), reflection spectra are appreciably different.

In a nanomechanics model, the continuum stresses are directly derived from micro level physical and geometrical parameters such as $A_{\alpha\beta}$, $\tau$'s and $\eta$. Thus, the macro level observable and/or measurable (e.g., reflection coefficients from the thin layer) are directly related to micro level parameters. The expressions for the displacement of waves in the system can be written in the following format:

Incident S wave:

$$u^{(0)} = \begin{Bmatrix} u_1^{(0)} \\ u_2^{(0)} \end{Bmatrix} = \begin{Bmatrix} A_0 \cos\theta_0 \exp(ik_0(x_1\sin\theta_0 - x_2\cos\theta_0 - c_0 t)) \\ A_0 \sin\theta_0 \exp(ik_0(x_1\sin\theta_0 - x_2\cos\theta_0 - c_0 t)) \end{Bmatrix}$$

Incident P wave:

$$u^{(0)} = \begin{Bmatrix} u_1^{(0)} \\ u_2^{(0)} \end{Bmatrix} = \begin{Bmatrix} A_0\sin\theta_0\exp(ik_0(x_1\sin\theta_0 - x_2\cos\theta_0 - c_0 t)) \\ A_0\cos\theta_0\exp(ik_0(x_1\sin\theta_0 - x_2\cos\theta_0 - c_0 t)) \end{Bmatrix}$$

Reflected S wave:

$$u^{(1)} = \begin{Bmatrix} u_1^{(1)} \\ u_2^{(1)} \end{Bmatrix} = \begin{Bmatrix} -A_1\cos\theta_1\exp(ik_1(x_1\sin\theta_1 + x_2\cos\theta_1 - c_1 t)) \\ A_1\sin\theta_1\exp(ik_1(x_1\sin\theta_1 + x_2\cos\theta_1 - c_1 t)) \end{Bmatrix}$$

Reflected P wave:

$$u^{(2)} = \begin{Bmatrix} u_1^{(2)} \\ u_2^{(2)} \end{Bmatrix} = \begin{Bmatrix} A_2\sin\theta_2\exp(ik_2(x_1\sin\theta_2 + x_2\cos\theta_2 - c_2 t)) \\ A_2\cos\theta_2\exp(ik_2(x_1\sin\theta_2 + x_2\cos\theta_2 - c_2 t)) \end{Bmatrix}$$

Transmitted S wave in layer:

$$u^{(3)} = \begin{Bmatrix} u_1^{(3)} \\ u_2^{(3)} \end{Bmatrix} = \begin{Bmatrix} A_3\cos\theta_3\exp(ik_3(x_1\sin\theta_3 - x_2\cos\theta_3 - c_3 t)) \\ A_3\sin\theta_3\exp(ik_3(x_1\sin\theta_3 - x_2\cos\theta_3 - c_3 t)) \end{Bmatrix}$$

Transmitted P wave in layer:

$$u^{(4)} = \begin{Bmatrix} u_1^{(4)} \\ u_2^{(4)} \end{Bmatrix} = \begin{Bmatrix} A_4\sin\theta_4\exp(ik_4(x_1\sin\theta_4 - x_2\cos\theta_4 - c_4 t)) \\ -A_4\cos\theta_4\exp(ik_4(x_1\sin\theta_4 - x_2\cos\theta_4 - c_4 t)) \end{Bmatrix}$$

Reflected S wave in layer:

$$u^{(5)} = \begin{Bmatrix} u_1^{(5)} \\ u_2^{(5)} \end{Bmatrix} = \begin{Bmatrix} -A_5\cos\theta_3\exp(ik_3(x_1\sin\theta_3 + x_2\cos\theta_3 - c_3 t)) \\ A_5\sin\theta_3\exp(ik_3(x_1\sin\theta_3 + x_2\cos\theta_3 - c_3 t)) \end{Bmatrix}$$

Reflected P wave in layer:

$$u^{(6)} = \begin{Bmatrix} u_1^{(6)} \\ u_2^{(6)} \end{Bmatrix} = \begin{Bmatrix} A_6\sin\theta_4\exp(ik_4(x_1\sin\theta_4 + x_2\cos\theta_4 - c_4 t)) \\ A_6\cos\theta_4\exp(ik_4(x_1\sin\theta_4 + x_2\cos\theta_4 - c_4 t)) \end{Bmatrix}$$

Transmitted S wave:

$$u^{(7)} = \begin{Bmatrix} u_1^{(7)} \\ u_2^{(7)} \end{Bmatrix} = \begin{Bmatrix} A_7\cos\theta_0\exp(ik_0(x_1\sin\theta_0 - x_2\cos\theta_0 - c_0 t)) \\ A_7\sin\theta_0\exp(ik_0(x_1\sin\theta_0 - x_2\cos\theta_0 - c_0 t)) \end{Bmatrix}$$

Transmitted P wave:

$$u^{(8)} = \begin{Bmatrix} u_1^{(8)} \\ u_2^{(8)} \end{Bmatrix} = \begin{Bmatrix} A_8\sin\theta_2\exp(ik_2(x_1\sin\theta_2 - x_2\cos\theta_2 - c_2 t)) \\ -A_8\cos\theta_2\exp(ik_2(x_1\sin\theta_2 - x_2\cos\theta_2 - c_2 t)) \end{Bmatrix}$$

where $u_i^{(j)}$ is the displacement associated with the (j)th wave that propagates along $x_i$ axis.

The reflection coefficients may be solved for by enforcing the following continuity conditions at $x_2=0$ (Equations (A)-(D)) and $x_2=d$ (Equations (E)-(H)):

Continuity of normal displacement at $x_2=0$:

$$u_1^{(0)}+u_1^{(1)}+u_1^{(2)}=u_1^{(3)}+u_1^{(4)}+u_1^{(5)}+u_1^{(6)} \quad (A)$$

Continuity of normal stress at $x_2=0$:

$$\sigma_{22}^{(0)}+\sigma_{22}^{(1)}+\sigma_{22}^{(2)}=\sigma_{22}^{(3)}+\sigma_{22}^{(4)}+\sigma_{22}^{(5)}+\sigma_{22}^{(6)} \quad (B)$$

Continuity of shear displacement at $x_2=0$:

$$u_2^{(0)}+u_2^{(1)}+u_2^{(2)}=u_2^{(3)}+u_2^{(4)}+u_2^{(5)}+u_2^{(6)} \quad (C)$$

Continuity of shear stress at $x_2=0$:

$$\sigma_{21}^{(0)}+\sigma_{21}^{(1)}+\sigma_{21}^{(2)}=\sigma_{21}^{(3)}+\sigma_{21}^{(4)}+\sigma_{21}^{(5)}+\sigma_{21}^{(6)} \quad (D)$$

Continuity of normal displacement at $x_2=-d$:

$$u_1^{(7)}+u_1^{(8)}=u_1^{(3)}+u_1^{(4)}+u_1^{(5)}+u_1^{(6)} \quad (E)$$

Continuity of normal stress at $x_2=-d$:

$$\sigma_{22}^{(7)}+\sigma_{22}^{(8)}=\sigma_{22}^{(3)}+\sigma_{22}^{(4)}+\sigma_{22}^{(5)}+\sigma_{22}^{(6)} \quad (F)$$

Continuity of shear displacement at $x_2=-d$:

$$u_2^{(7)}+u_2^{(8)}=u_2^{(3)}+u_2^{(4)}+u_2^{(5)}+u_2^{(6)} \quad (G)$$

Continuity of shear stress at $x_2=-d$:

$$\sigma_{21}^{(7)}+\sigma_{21}^{(8)}=\sigma_{21}^{(3)}+\sigma_{21}^{(4)}+\sigma_{21}^{(5)}+\sigma_{21}^{(6)} \quad (H)$$

where $\sigma^{(n)}_{ij}$ is the stress associated with the nth wave and $u^{(n)}_m$ is the displacement associated with the nth wave. The above boundary conditions give an 8×8 matrix by which the reflection coefficients ($R_L$ or $R_S$) can be solved for assuming the incident wave 300 and the material properties of the substrate and the thin layer are known. Once the reflection coefficients have been solved for, they can be stored in a computer data store, alone and/or with other wave and/or tissue data, in a model. The model facilitates distinguishing tissue based on their reflection properties (e.g., coefficients, spectra).

Numerical solutions for a nanomechanics modeling problem can be obtained by employing the example arrangement illustrated in FIG. 5. This sample arrangement results in three dimensional macroscopic isotropy if the order of the scale is chosen to be one (M=1). It also reduces the number of the independent micromoduli in the example to two: $A_{11}$ and $A_{44}$.

Given the arrangement in FIG. 5, a direction cosine matrix can be computed:

$$\tau_1=(1,0,0) \quad \tau_4=(0,1/\sqrt{2},1/\sqrt{2})$$

$$\tau_2=(0,1,0) \quad \tau_5=(1/\sqrt{2},0,1/\sqrt{2})$$

$$\tau_3=(1,0,0) \quad \tau_6=(1/\sqrt{2},1/\sqrt{2},0)$$

The micromoduli of a tissue are estimated from macro elastic moduli based on the fact that the multi-scale model reduces to the continuum model when the scale factor is equal to one. The micromoduli are related to Lame's constants as follows:

$$\lambda = A_{11} - A_{44}$$

$$\mu = \frac{1}{4}A_{44}$$

In one example, the values of the macro elastic moduli of the thin tissue layer were adopted from the averaged values for human breast tissue. In the example, it was also hypothesized that the dimension of the nodes in the discrete model for the biological tissue corresponds to that of the cells. Additionally, the example assumed that the cells were close-packed so that the internodal distance was equivalent to the cell diameter. The typical dimension of human breast epithelial cells is at the 10-µm scale. The example further assumed that the internodal distances were the same for substantially all doublets. Therefore η is at the scale of 10-µm. Therefore, in one example it can be assumed that the set of parameters for the biological tissue thin layer as follows:

Density: 1.0 g/cm³
$A_{11}$=3.0 GPa
$A_{44}$=0.5 GPa
η=1~10-µm

In one example, the thickness of the thin layer was assumed to be 150-µm, which is thin enough to be considered a "thin" layer compared to the dimension of the substrates (glass slides) and thick enough to accommodate several nodes (cells) cross the thickness. The incident angle can be a variety of arbitrary angles if the angle's magnitude is between those of the two mode conversion angles for the glass-tissue interface.

Figure 9:
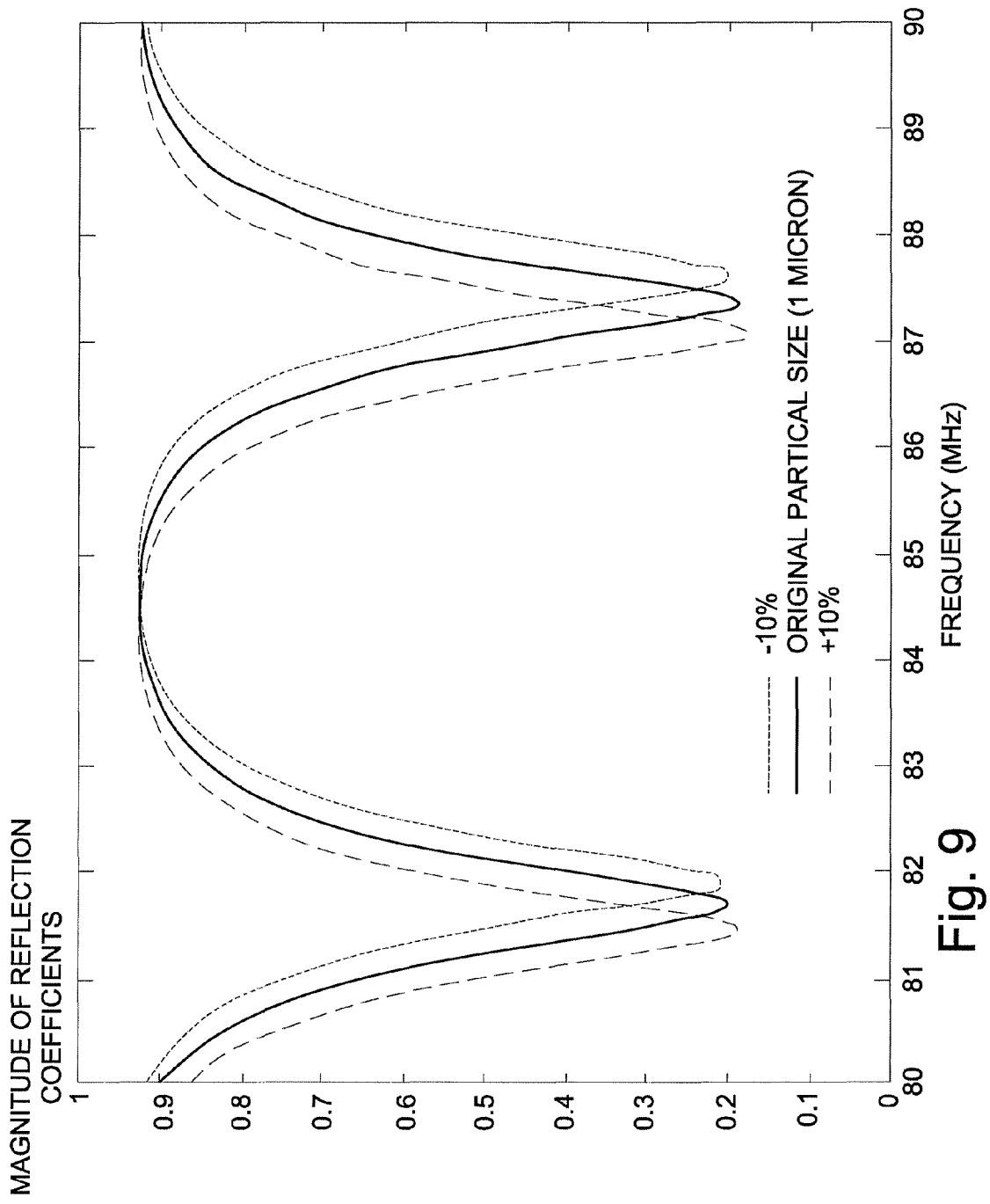
FIG. 9 illustrates an effect on mechanical response due to varying particle size to facilitate studying reflection spectra.

The nanomechanics model offers the opportunity to correlate the response of a medium to its microstructural characteristics. For example, if the size of the particles is varied while other properties remain the same, a change in the reflection coefficient is observed, as illustrated in FIG. 9. Thus, the nanomechanics model gives insight to the upper limit of the size of the particles before they become "visible" for elastic waves propagating at a certain range of frequencies.

Figure 7:
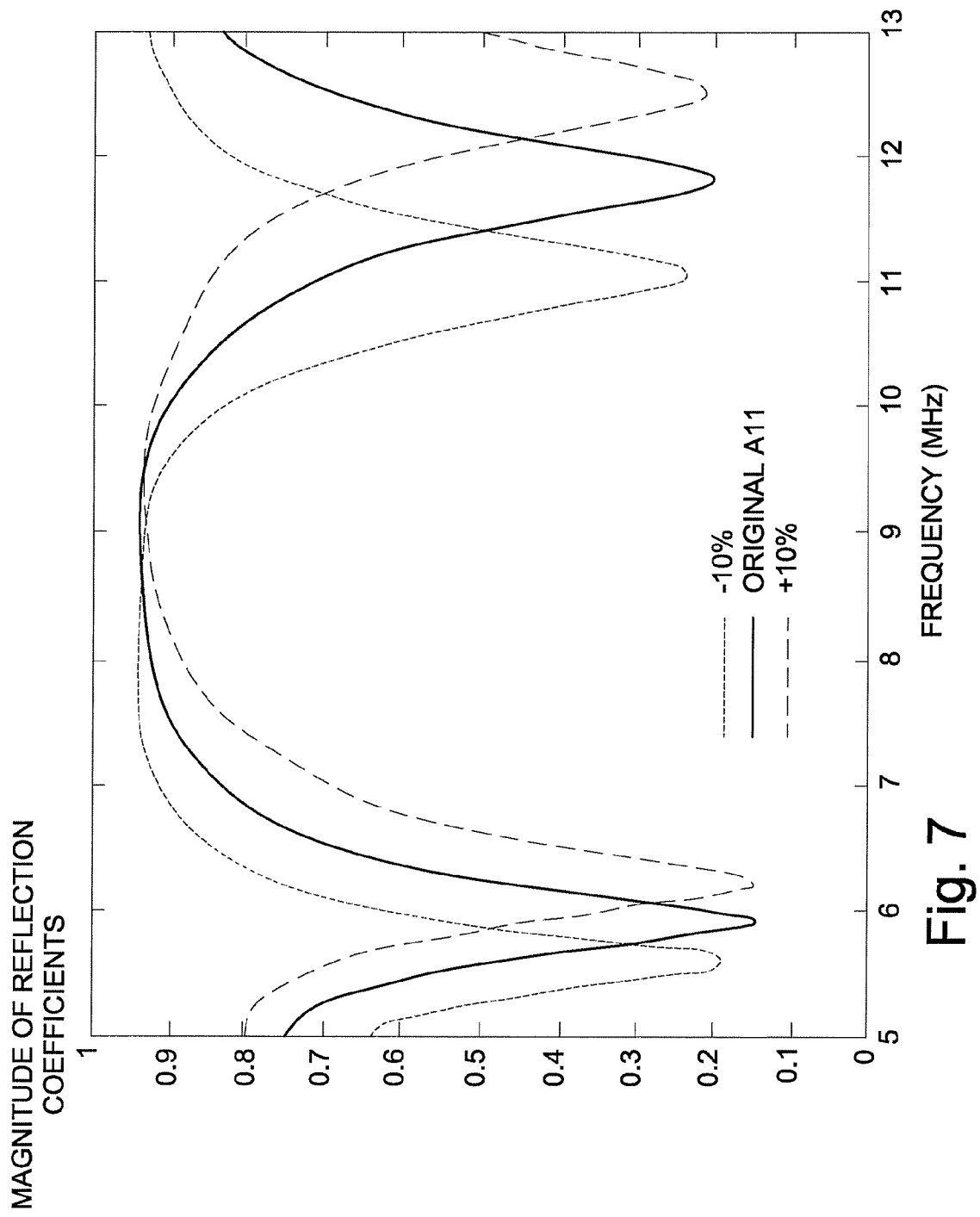
FIG. 7 illustrates an effect on mechanical response due to varying $A_{11}$ to facilitate studying the reflection spectra.
Figure 8:
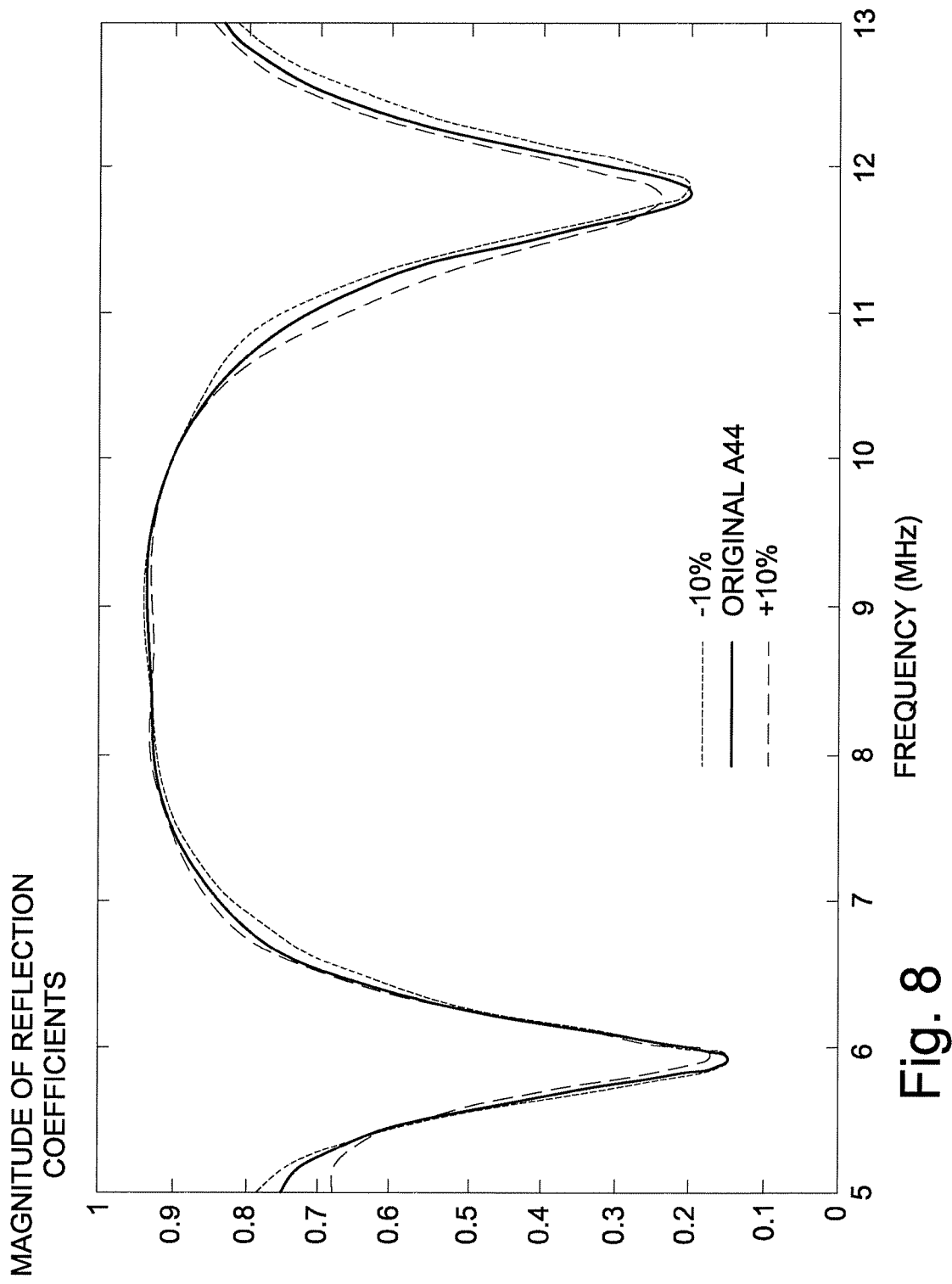
FIG. 8 illustrates an effect on mechanical response due to varying $A_{44}$ to facilitate studying the reflection spectra.

In one experiment, with other parameters fixed, a micromodulus $A_{\alpha\beta}$ (e.g., $A_{11}$) is varied to study its effect on the reflection spectrum. FIG. 7 illustrates that an increase in micromodulus $A_{11}$ results in shifting of the overall spectrum to the right (higher frequency), and vice versa. The changes in micromodulus $A_{11}$ change the location of the minima in the curves. Nevertheless, the magnitude of the minima and the distance between the minima remain unaffected. Similarly the effect of changing another modulus $A_{\alpha\beta}$ (e.g., $A_{44}$) is studied by varying its magnitude. The result is shown in FIG. 8. FIG. 8 shows that $A_{44}$ affects the overall reflection spectra less than compared to $A_{11}$. In other words, $A_{44}$ is a less sensitive parameter in terms of determining the reflection spectrum. But, FIG. 8 does show that increase in micromodulus $A_{44}$ results in shifting of the second minimum to the left (lower frequency), and vice versa. Therefore changes in micromodulus $A_{44}$ change the distance between the two minima, and also the magnitude of the minima. Therefore, systems and methods for screening tissue can employ a response model that stores information associated with micromodulus changes to facilitate screening for (un)healthy tissue.

While the micromodulus effects on reflected waves can be employed to distinguish tissue, so too can the effects on reflected waves due to particle size, or internodal distance related to cell size and micro-architecture be employed to distinguish tissue. In one experiment employed to develop a model, the particle size of the thin layer is varied to study its effect on the reflection spectrum and to facilitate solving for reflection coefficients. These properties (e.g., micromodulus, particle size) affect the reflection spectra. The reflection spectra are fully defined by the properties of the tissue. Therefore, the properties can be determined through inversion from the experimental data in combination with a response model.

At higher frequency ranges (e.g., ultrasonic) particle size has an effect on the reflection spectrum by shifting it to the left with increased magnitude of the particle size as illustrated in FIG. 9. This effect is similar to that of micromodulus $A_{11}$, however, the effects of the two parameters differ. Changes in micromodulus $A_{11}$ have the same effect on the reflection spectra regardless of the frequency range, while the effect of particle size is frequency dependent.

Figure 10:
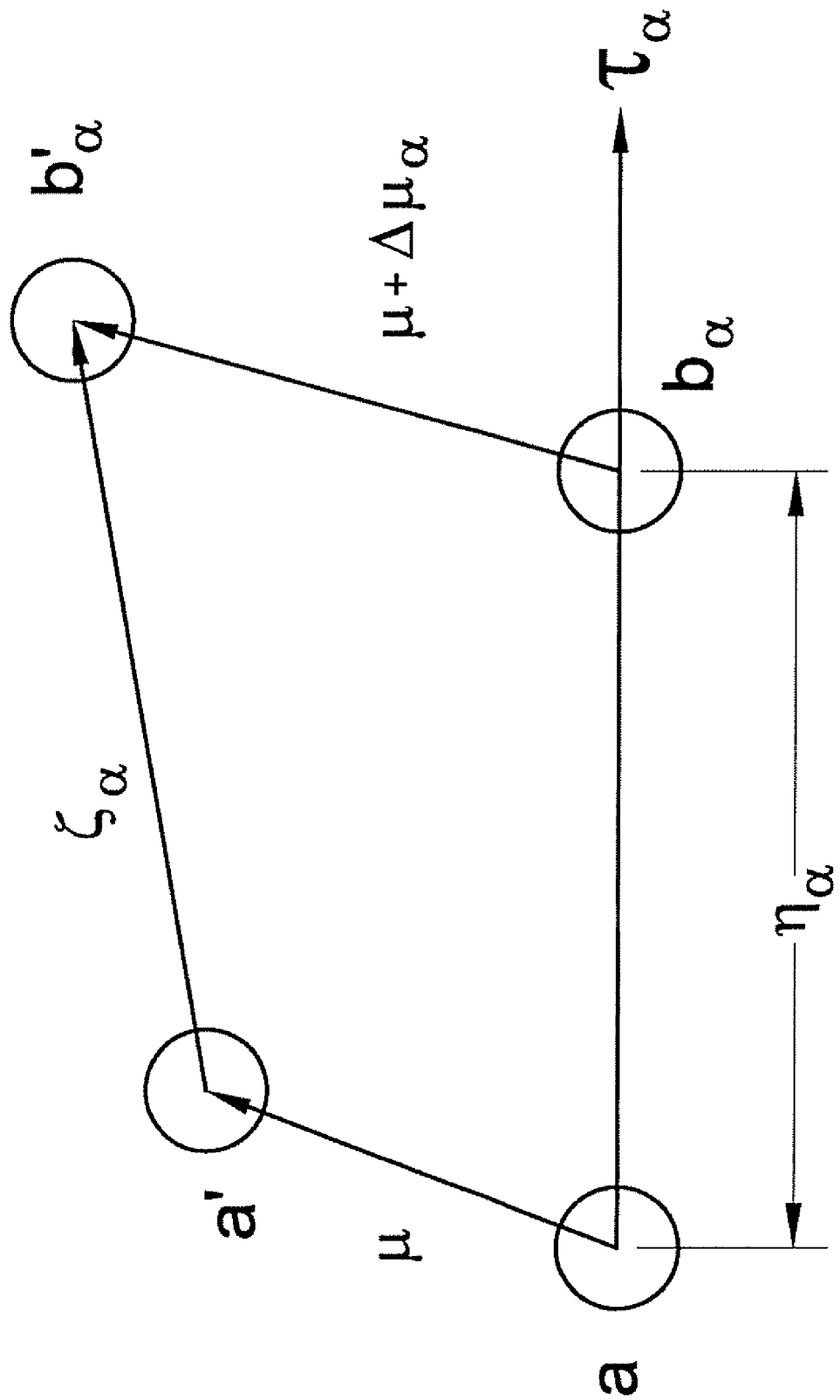
FIG. 10 illustrates an example translation of doublet nodes as characterized in nanomechanics.

FIG. 10 illustrates translations of the doublet nodes a and $b_\alpha$. $\eta_\alpha$ is the distance between the two doublet nodes, $\tau_\alpha$ is the unit vector along the original direction from node a to $b_\alpha$, and $\zeta_\alpha$ is the new direction vector after the deformation. The nanomechanical model assumes that particle displacements vary little at the lengths on the order of their separations. Thus, in one example model, a smooth vector field of the translation function u(X,t) is employed, where X is the position vector of an arbitrary point in the body and t is time. The vector field of the translation displacement is assumed to coincide with the real translation of the granular body particles at the node α, where X=x.

An incremental vector $\Delta u_\alpha$ is introduced, which is defined as:

$$\Delta u_\alpha = u(x+\zeta_\alpha, t) - u(x,t)$$

which represents an increment of the translation vector u in a transition from an arbitrary node a to the adjacent node $b_\alpha$. The increment vector may be expanded in a convergent Taylor series in a neighborhood of an arbitrary node a whose position vector is x. Truncating this series at the M-th term yields:

$$\Delta u_\alpha = \sum_{\chi=1}^{M} \frac{(\eta_\alpha)^\chi}{\chi!} (\tau_\alpha \cdot \nabla)^\chi u(x,t)$$

when X=x.
Based on the above assumptions, the axial microstrain is:

$$\varepsilon_\alpha = \tau_{\alpha i} \sum_{\chi=1}^{M} \frac{(\eta_\alpha)^{\chi-1}}{\chi!} \tau_{\alpha k_1} \cdots \tau_{\alpha k_\chi} \frac{\partial^\chi u_i}{\partial x_{k_1} \cdots \partial x_{k_\chi}}$$

Thus, the first approximation (M=1) for the axial microstrain takes the form:

$$\epsilon_\alpha = \tau_{\alpha i} \tau_{\alpha j} \epsilon_{ij}$$

where $$\varepsilon_{ij} = \frac{1}{2}\left(\frac{\partial u_i}{\partial x_j} + \frac{\partial u_j}{\partial x_i}\right)$$

And the second approximation (M=2) takes the form:

$$\varepsilon_\alpha = \tau_{\alpha i}\tau_{\alpha j}\frac{\partial u_i}{\partial x_j} + \frac{1}{2}\eta_\alpha \tau_{\alpha i}\tau_{\alpha j}\tau_{\alpha k}\frac{\partial^2 u_i}{\partial x_j \partial x_k}$$

in expansion, it becomes:

$$\varepsilon_\alpha = \tau_{\alpha 1}^2 \frac{\partial u_1}{\partial x_1} + \tau_{\alpha 1}\tau_{\alpha 2}\left(\frac{\partial u_1}{\partial x_2} + \frac{\partial u_2}{\partial x_1}\right) + \tau_{\alpha 2}^2 \frac{\partial u_2}{\partial x_2} +$$
$$\frac{\eta_\alpha}{2}\left(\tau_{\alpha 1}^3 \frac{\partial^2 u_1}{\partial x_1^2} + 2\tau_{\alpha 1}^2 \tau_{\alpha 2}\frac{\partial^2 u_1}{\partial x_1 \partial x_2} + \tau_{\alpha 2}^2 \tau_{\alpha 1}\frac{\partial^2 u_1}{\partial x_2^2} + \right.$$

$$\tau_{\alpha 1}^2 \tau_{\alpha 2}^2 \frac{\partial^2 u_2}{\partial x_1^2} + 2\tau_{\alpha 2}^2 \tau_{\alpha 1} \frac{\partial^2 u_2}{\partial x_1 \partial x_2} + \tau_{\alpha 2}^3 \frac{\partial^2 u_2}{\partial x_2^2}\Bigg)$$

Thus, microstress pa that is associated with $\epsilon_\alpha$ is defined and a microstress-microstrain constitutive relationship can be examined via:

$$p_\alpha = \sum_{\beta=1}^n A_{\alpha\beta} \varepsilon_\beta$$

where $A_{\alpha\beta}$ are the micro-level elastic moduli. The transition from microstresses to macrostresses is achieved by applying equilibrium equations and the resulting relationship is:

$$\sigma_{k_1 i}^{(M)} = \sum_{\alpha=1}^n \tau_{\alpha k_1} \sum_{\chi=1}^M (-1)^{\chi+1} \frac{(\eta_\alpha)^{\chi-1}}{\chi!}$$

$$\tau_{\alpha k_2} \cdots \tau_{\alpha k_\chi} \frac{\partial^{\chi-1}(p_{\alpha i})}{\partial x_{k_2} \cdots \partial x_{k_\chi}}$$

The first approximation (M=1) for stress takes the form:

$$\sigma_{ij} = \sum_{\alpha=1}^n \tau_{\alpha j} \tau_{\alpha i} p_\alpha$$

It is further derived that the macromoduli for the M=1 case becomes:

$$C_{ijkl} = \sum_{\alpha,\beta=1}^n A_{\alpha\beta} \tau_{\alpha i} \tau_{\alpha j} \tau_{\beta k} \tau_{\beta l}$$

The second approximation (M=2) for continuum stress takes the form:

$$\sigma_{ij} = \sum_{\alpha=1}^n \tau_{\alpha j}\left(\tau_{\alpha i} p_\alpha - \frac{1}{2}\eta_\alpha \tau_{\alpha k} \tau_{\alpha k} \frac{\partial p_\alpha}{\partial x_k}\right)$$

Thus, systems and methods that screen tissue, substantially in real-time, can rely on a reflection coefficients and/or biomechanical response model based on the approximations, equations, assumptions, and experimental results detailed above. It is to be appreciated that the approximations, equations, assumptions and experimental results described above illustrate examples that can be employed to characterize the mechanical response of tissue to ultrasonic waves. Accordingly, other systems that rely on other models that characterize the mechanical response of tissue to ultrasonic waves, where the models are based on solving for reflective coefficients and nanomechanics are contemplated. In one example, a tissue mechanical properties model stores information concerning one or more of, tissue reflection, tissue transmission, tissue elasticity, tissue particle size, tissue micromoduli, tissue micro-architecture, and tissue mechanical responses.

Figure 11:
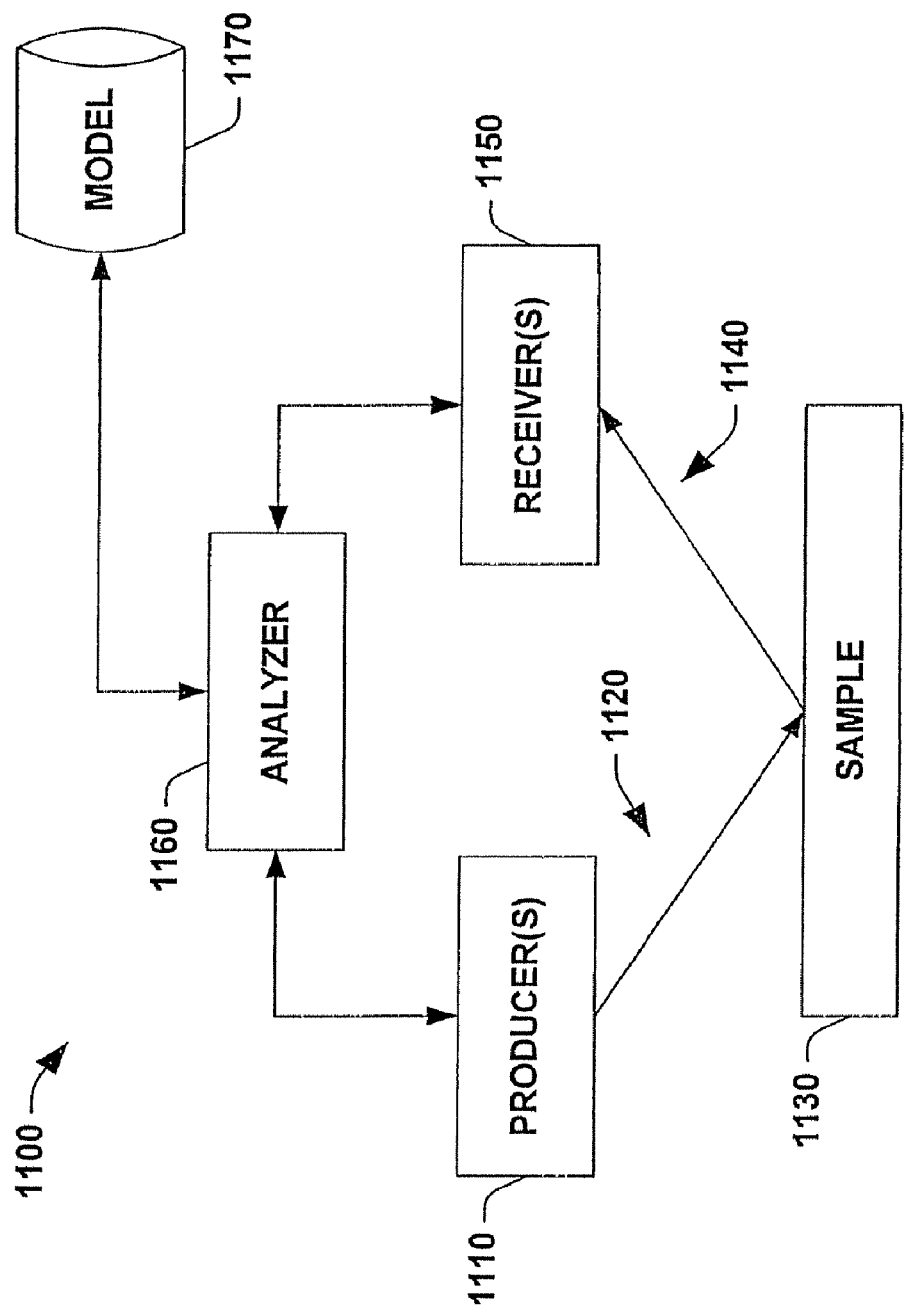
FIG. 11 illustrates an example system for screening tissue.

One sample tissue screening system 1100 is illustrated in FIG. 11. The system 1100 includes an ultrasonic wave producer 1110 that produces an ultrasonic wave 1120 that is directed at a tissue sample 1130 that is to be screened. The system 1100 also includes an ultrasonic wave receiver 1150 that receives ultrasonic waves 1140. The ultrasonic waves 1140 are produced by the ultrasonic wave 1120 interacting with the tissue sample 1130. Thus the waves 1140 can be, for example, reflected and/or transmitted waves. As described above, different tissues with different mechanical properties due to their state of (un)healthiness will interact differently with incident waves and lead to differences in reflected waves, which facilitates screening for diseased tissue. The system 1100 also includes an analyzer 1160 operably connected to the ultrasonic wave producer 1110 and/or the ultrasonic wave receiver 1150. The analyzer 1160 differentiates tissue regions in the tissue sample 1130 by, at least in part, analyzing one or more parameters of the ultrasonic waves 1140 and/or the ultrasonic waves 1120. For example, the analyzer 1160 may analyze one or more of an incident angle of wave 1120, a reflected angle of wave 1140, a reflection spectrum, and/or a relationship between them. While the example system 1100 has one producer 1110, one receiver 1150, and one analyzer 1160 illustrated, it is to be appreciated that a greater number of such components can be employed in other examples. In one example, the analyzer 1160 is a computer component.

In one example, the system 1100 can include a tissue mechanical properties model 1170 in data communication with the analyzer 1160. The tissue mechanical properties model 1170 can store information concerning, but not limited to, tissue reflection, tissue transmission, tissue elasticity, tissue particle size, tissue micromoduli, tissue micro-architecture, and reflection coefficients of normal and abnormal tissues. The model 1170 can be based on theories including, but not limited to, nanomechanics. The tissue sample 1130 can be, for example, from an external tissue surface (e.g., skin), an internal tissue surface (e.g., stomach lining), human tissue, animal tissue, and so on.

Figure 12:
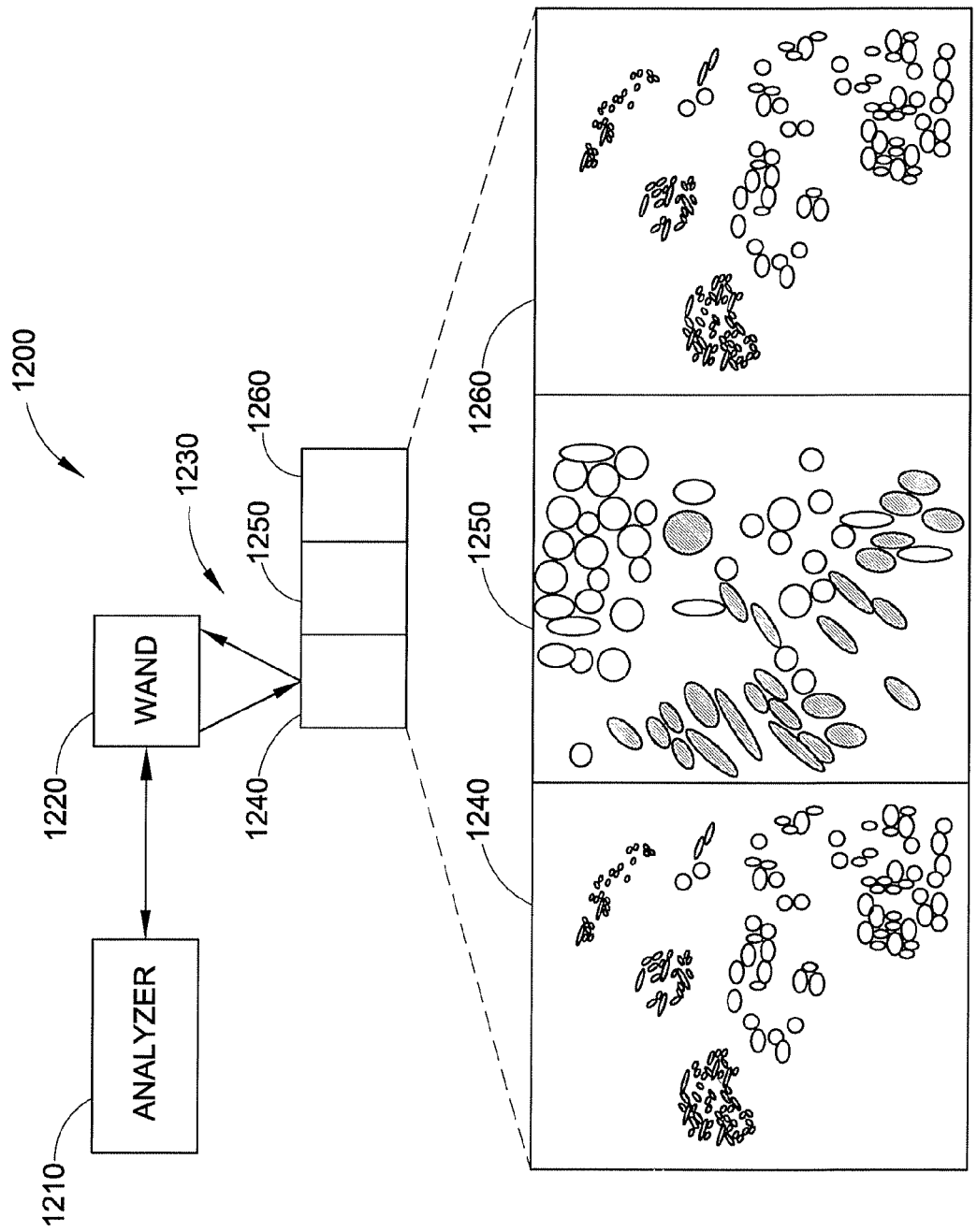
FIG. 12 illustrates an example system for screening tissue.

Another example system 1200 is illustrated in FIG. 12. The system 1200 includes a wand 1220 that can be passed over a tissue sample. The tissue sample is illustrated as having three representative sections, 1240, 1250 and 1260. As can be seen, sections 1240 and 1260 are normal, healthy tissue, and are likely to produce a similar set of reflected waves due to their similar nanomechanical properties. However, section 1250 is illustrated as being affected by a malignant disease (e.g., invasive ductal carcinoma), and thus will likely produce a set of reflected waves that differ from those produced when the wand 1220 sends waves 1230 over sections 1240 and 1260. Thus, reflected waves received by the wand 1220 may be processed by an analyzer 1210 that can identify the locations in the tissue sample where the reflected waves changed from one set of properties to a second set and back again. Based on such analysis and identification, a pathologically interesting area can be tagged for subsequent analysis. The tagging can include, but is not limited to, recording coordinates of the tissue where the waves changed, changing the physical appearance of an image generated from the reflected waves, raising an alarm so that an operator can manually mark the location of the changes, and so on. It is to be appreciated that other approaches to "tagging" an identified tissue area can be employed in accordance with aspects of the systems and methods described herein. While FIG. 12 illustrates a wand 1220 being passed over a tissue sample, it is to be appreciated that other physical arrangements of wave transmitter/receiver and tissue sample can be employed in accordance with aspects of the present invention. For example, a portable system may be arranged so that a patient could pass a tissue area (e.g., mole on hand) over the system, or a portable system may be arranged so that it can be passed over a tissue area (e.g., breast).

In one example, the tissue may be treated with a nanoparticle contrast agent. The nanoparticle contrast agent can be prepared so that a higher concentration of the agent would localize in, for example, section 1250, with a lower concentration in sections 1240 and 1260. Thus, the analyzer 1210 could more easily distinguish healthy from malignant tissue.

Figure 13:
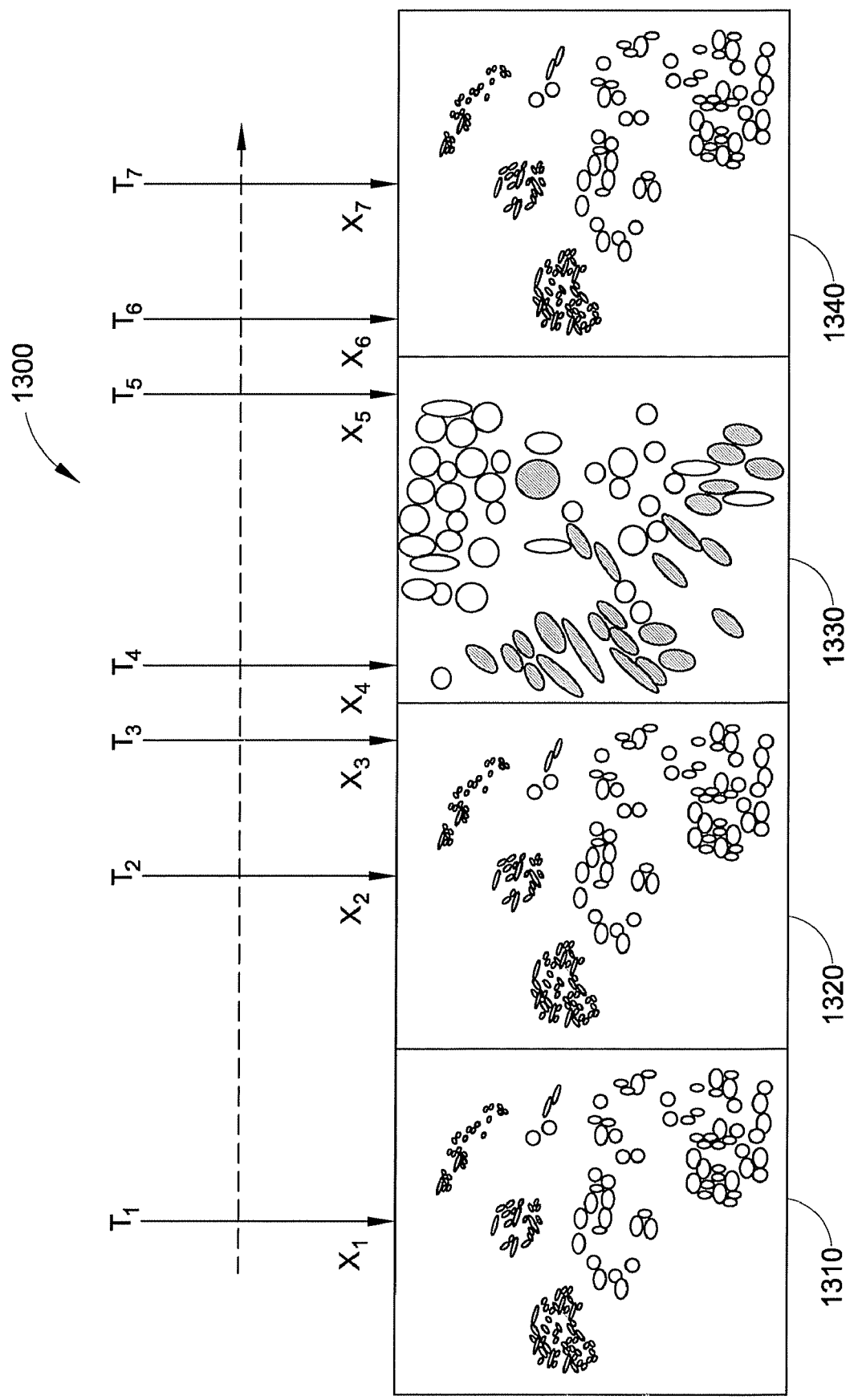
FIG. 13 illustrates example sampling times and locations employed in a method for screening tissue.

FIG. 13 illustrates a series 1300 of example sampling times and locations employed in a method for screening tissue. At a first time $T_1$, a wave generator may be positioned so that a first wave is directed at a sample 1310 at a location $X_1$. Later, at a second time $T_2$, the wave generator may be positioned (or the tissue may be moved) so that a second wave is directed at a sample 1320 at a location $X_2$. Similarly, tissue may be sampled at other times (e.g., $T_3$ through $T_7$) and other locations (e.g., $X_3$ through $X_7$). As described above, the reflection of the waves is likely to differ based on the mechanical properties of the tissue with which the wave interacts. Thus, as the tissue is scanned from left to right, an analyzer could identify the location of reflection changes, which facilitates marking pathologically interesting areas. Furthermore, if the waves received at various times and locations is stored, then when the same tissue sample is analyzed at a later point in time, differences between waves, and changes between reflections, can be identified. This facilitates, for example, tracking mole growth.

While the waves are illustrated being directed normal to the surface of the tissue sample, it is to be appreciated that the waves may be directed at various angles. For example, waves may be directed at a tissue sample located between glass slides immersed in water so that the incident angle is an angle between the two mode conversion angles of the glass slides and the fluid in which the slide is immersed. Or, in another example, the incident angle may be between 15 and 20 degrees. Furthermore, waves of various frequencies can be employed. For example, a first ultrasonic pulse may be in the range of 2.5 to 12.5 MHz, with a central frequency of 7.5 MHz, while another ultrasonic wave may be in the range of about 7 to about 13 MHz.

Figure 14:
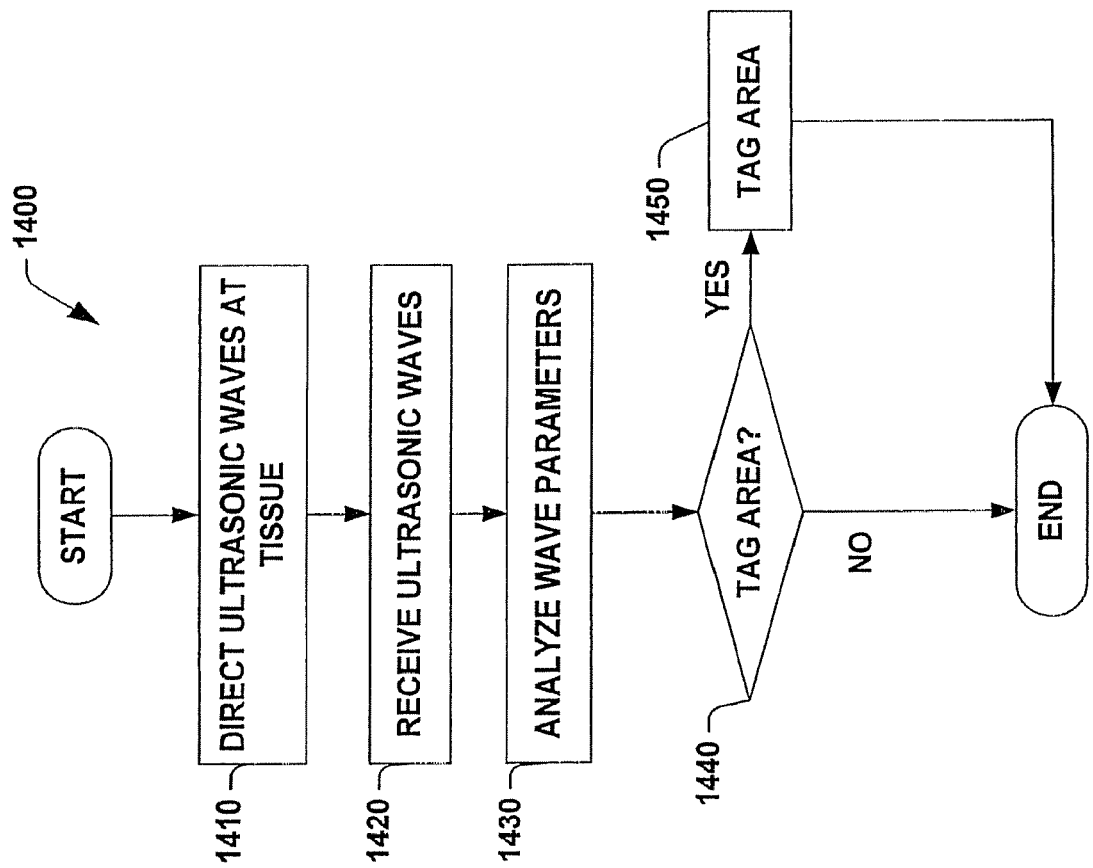
FIG. 14 illustrates an example method for screening tissue using ultrasonic waves.
Figure 15:
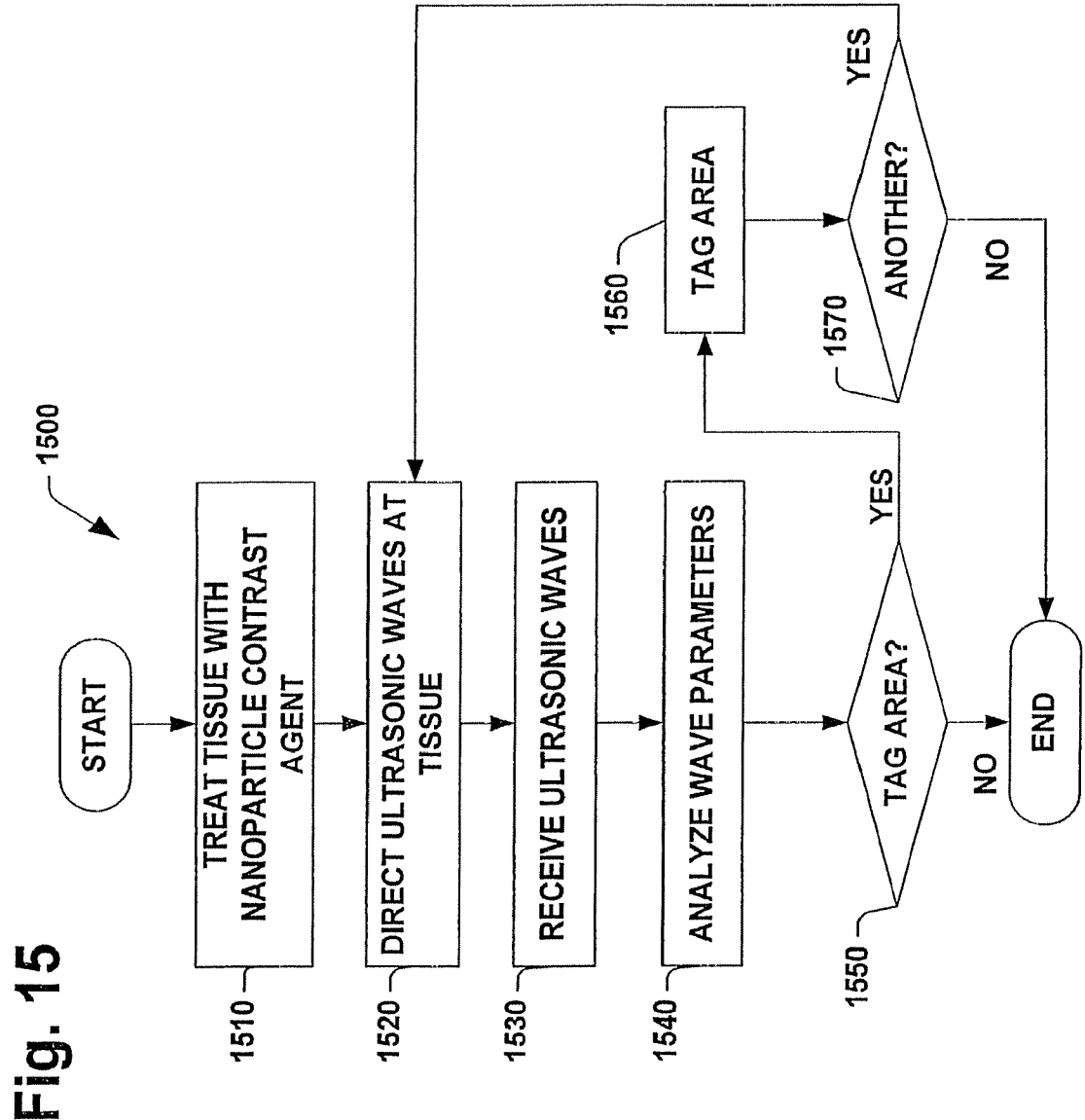
FIG. 15 illustrates another example method for screening tissue using ultrasonic waves.
Figure 16:
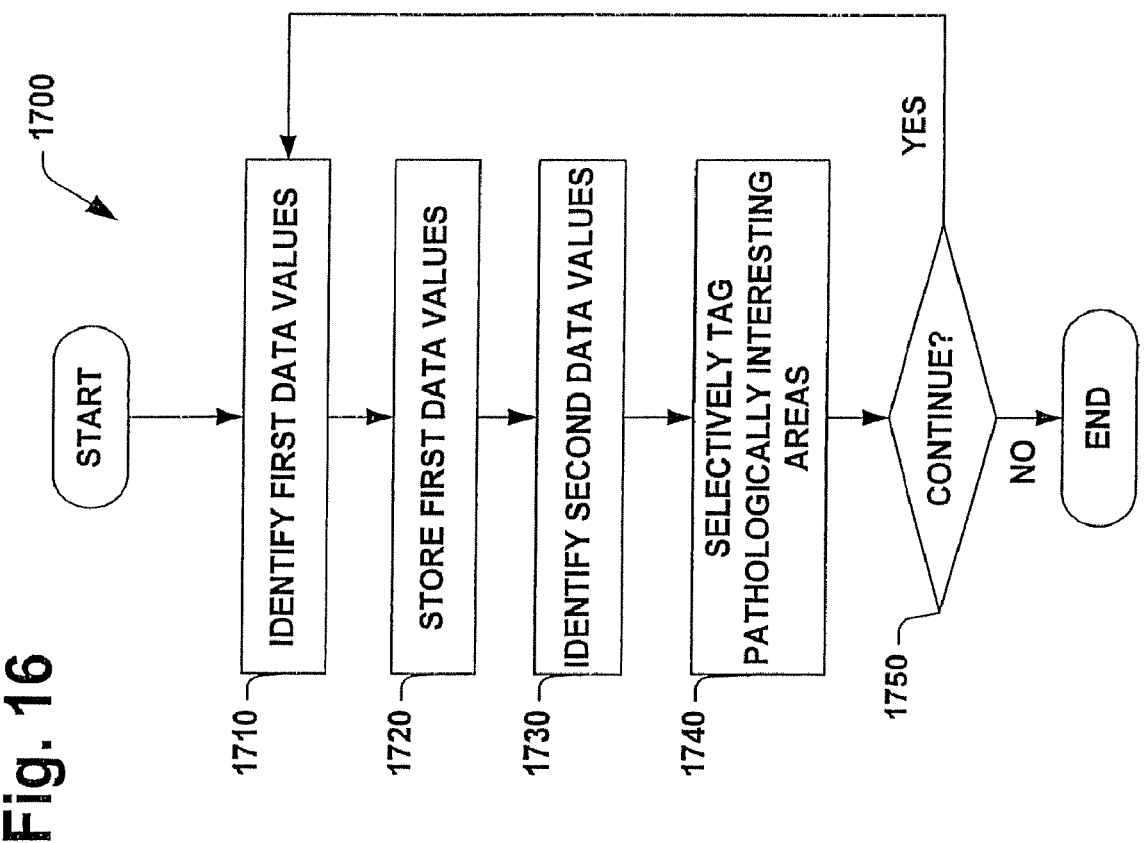
FIG. 16 illustrates an example method for mapping tissue areas using ultrasonic waves.

In view of the exemplary systems shown and described herein, example methodologies that are implemented will be better appreciated with reference to the flow diagrams of FIGS. 14, 15, and 16. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Furthermore, additional and/or alternative methodologies can employ additional, not illustrated blocks. In one example, methodologies are implemented as computer executable instructions and/or operations, stored on computer readable media including, but not limited to an application specific integrated circuit (ASIC), a compact disc (CD), a digital versatile disk (DVD), a random access memory (RAM), a read only memory (ROM), a programmable read only memory (PROM), an electronically erasable programmable read only memory (EEPROM), a disk, a carrier wave, and a memory stick.

In the flow diagrams, rectangular blocks denote "processing blocks" that may be implemented, for example, in software. Similarly, the diamond shaped blocks denote "decision blocks" or "flow control blocks" that may also be implemented, for example, in software. Alternatively, and/or additionally, the processing and decision blocks can be implemented in functionally equivalent circuits like a digital signal processor (DSP), an ASIC, and the like.

A flow diagram does not depict syntax for any particular programming language, methodology, or style (e.g., procedural, object-oriented). Rather, a flow diagram illustrates functional information one skilled in the art may employ to program software, design circuits, and so on. It is to be appreciated that in some examples, program elements like temporary variables, routine loops, and so on are not shown.

FIG. 14 illustrates an example method 1400 for screening tissue. The method 1400 includes, at 1410, directing an ultrasonic wave at a tissue to be screened. The waves may be, for example, waves with frequencies between 3 and 13 MHz, with a center frequency of 8 MHz. It is to be appreciated that waves with other bandwidths and center frequencies can be employed in accordance with aspects of the present invention. The method 1400 includes, at 1420, receiving one or more second ultrasonic waves produced by the first ultrasonic wave interacting with the tissue to be screened. The second ultrasonic waves may include, for example, reflected waves, transmitted waves, and the like.

The method 1400 includes, at 1430, analyzing one or more parameters associated with the second ultrasonic waves in the context of a tissue mechanical properties model. The parameters can include, but are not limited to, tissue reflection, tissue transmission, tissue elasticity, tissue particle size, tissue micromoduli, tissue micro-architecture, and tissue mechanical response properties. Furthermore, the waves can be analyzed as they relate to the first ultrasonic waves of 1410.

The method 1400 also includes, at 1440, determining whether an area of the tissue to be screened should be tagged. Determining whether an area should be tagged may include analyzing the results of analyzing the wave parameters. If the determination at 1440 is YES, then at 1450, the area can be tagged, otherwise processing can conclude.

FIG. 15 illustrates an example method 1500 for screening tissue, where a nanoparticle contrast agent is associated with the tissue to be screened before an ultrasonic wave is directed at the tissue. The ability of a scanner being passed over a tissue area to detect a boundary between tissue with different mechanical characteristics can be enhanced by biologically targeted micro- or nano-particles. The particles can be employed as mechanical signal amplifiers, or nanomechanical 'smart contrast agents'. Particles may be conjugated to biologically targeting agents with pronounced affinity for molecular biomarkers associated with pathologies of interest. The particles facilitate maximizing nanomechanical contrast with respect to normal adjacent tissue, which in turn facilitates detecting the boundary between tissue with different mechanical characteristics.

At 1510, the tissue is treated with a nanoparticle contrast agent. By way of illustration, particles of certain sizes (e.g., <10 microns) may be injected intravenously. Tumor marker targeting nanoparticles in this size range may then be employed as ultrasound contrast agents for in vivo molecular imaging. In one example, particles may be coated with an antibody that targets a biomarker on a cancer and/or an angiogenic blood vessel, which facilitates concentrating the nanoparticles in pathologically interesting areas. The material of the particles could be bioglass and/or silicon, or other materials with a Young's modulus greater than normal and/or malignant tissue. In one example, the nanoparticles may also be void (e.g., with air inside) which will also enhance the contrast.

At 1520, an ultrasonic wave is directed at a tissue to be screened. The waves may be, for example, waves with frequencies between 3 and 13 MHz, with a center frequency of 8 MHz. It is to be appreciated that waves with other bandwidths and center frequencies can be employed in accordance with aspects of the present invention. The method 1500 includes, at 1530, receiving one or more second ultrasonic waves produced by the first ultrasonic wave interacting with the tissue to be screened. The second ultrasonic waves may include, for example, reflected waves, transmitted waves, and the like.

At 1540, the method 1500 includes analyzing wave parameters. The wave parameters can include, but are not limited to, tissue reflection, tissue transmission, tissue elasticity, tissue particle size, tissue micromoduli, tissue micro-architecture, and tissue mechanical response properties.

At 1550, the method 1500 also includes determining whether an area of the tissue to be screened should be tagged. If the determination at 1550 is YES, then at 1560 the area can be tagged. Subsequently, at 1570, a determination can be made concerning whether another area should be analyzed. If the determination is YES, then processing returns to 1520, otherwise processing can conclude.

FIG. 16 illustrates an example tissue area mapping method 1700. One example area that can be mapped is a mole. The method includes, at 1710, identifying first data values for a set of tissue area parameters. The first data values are acquired by processing a first resultant ultrasonic wave received from a tissue area, where the first resultant ultrasonic wave is the result of a first incident ultrasonic wave interacting with the tissue area. Thus, a first wave or set of waves is directed at a tissue sample, the resulting waves are acquired, and data values associated with the incident and/or reflected waves are generated. Then, at 1720, the first data values are stored.

At a later time, at 1730, the method 1700 includes identifying one or more second data values for the set of tissue area parameters. The second data values are acquired, for example, by directing ultrasonic waves at the same tissue sample and collecting reflected waves. Data values are then generated by processing the second resultant ultrasonic wave that is the result of a second incident ultrasonic wave interacting with the tissue area. In this way, two sets of data concerning the same tissue area can be acquired. This facilitates, for example, mole mapping, through comparing the first and second set of data values.

The method 1700 includes, at 1740, selectively tagging a pathologically interesting tissue location in the tissue area based, at least in part, on analyzing tissue mechanical properties discernible by analyzing one or more of the first data values, the second data values, and relations between the first and second data values. Thus, by comparing values acquired at a first point in time with values acquired at a second point in time, differences between the data values can be ascertained. These differences may indicate a pathologically significant event, and thus the area where the differences are noted may be tagged for further processing.

At 1750, a decision is made concerning whether to continue mapping an area. If the determination at 1750 is YES, then processing returns to 1710, otherwise processing can conclude. While two data sets are acquired in 1700, it is to be appreciated that a greater number of data sets can be acquired. While such data sets may be acquired at varying points in time, pathologically relevant periods of time (e.g. six months) may elapse between gathering the data sets.

In one example, analyzing the first data values and the second data values includes analyzing properties including, but not limited to, tissue reflection, tissue transmission, tissue elasticity, tissue particle size, tissue micromoduli, and tissue mechanical response properties.

Figure 17:
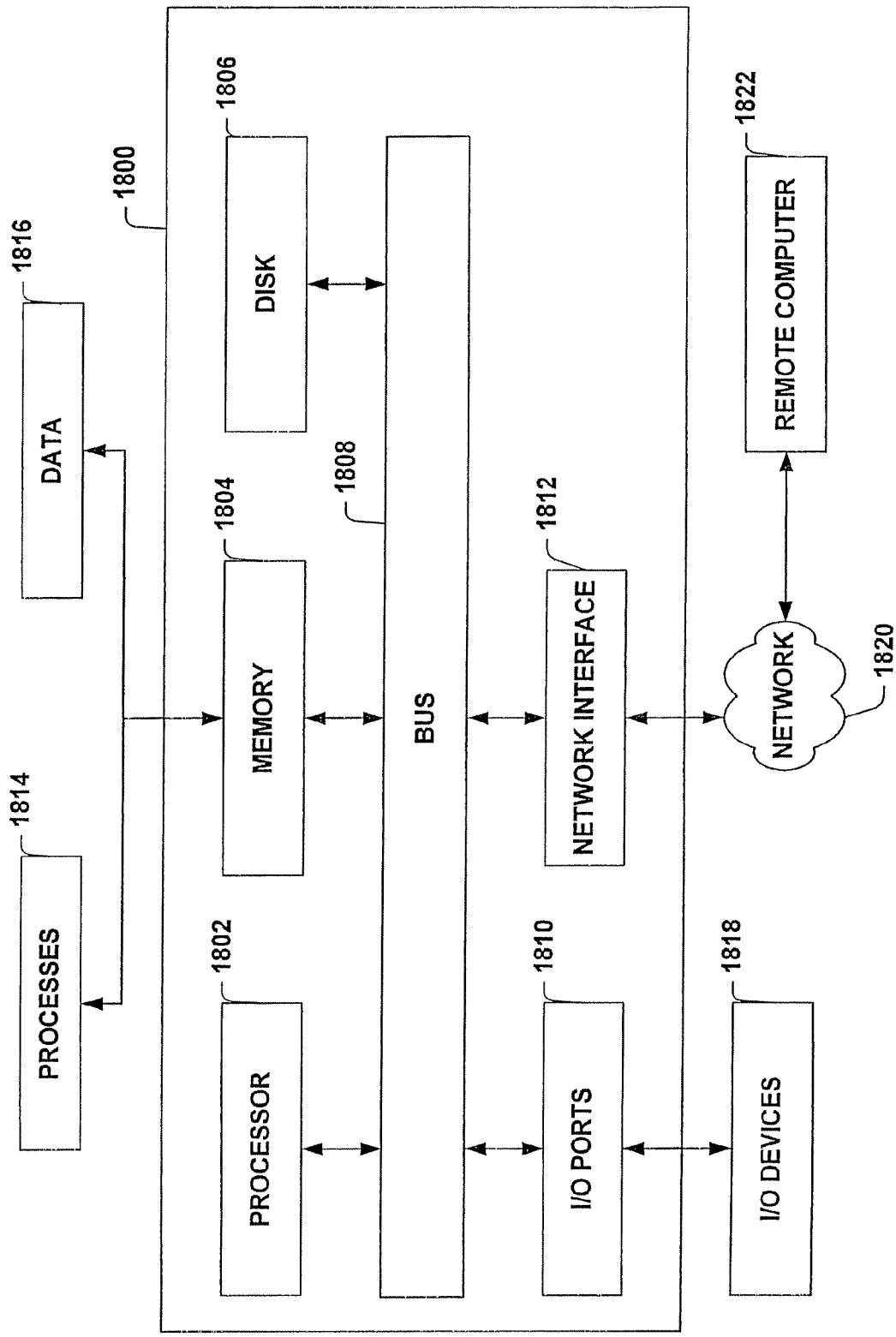
FIG. 17 is a schematic block diagram of an example computing environment with which computer executable portions of the systems and methods described herein can interact.

FIG. 17 illustrates a computer 1800 that includes a processor 1802, a memory 1804, a disk 1806, input/output ports 1810, and a network interface 1812 operably connected by a bus 1808. Executable components of the systems described herein may be located on a computer like computer 1800. Similarly, computer executable methods described herein may be performed on a computer like computer 1800. It is to be appreciated that other computers may also be employed with the systems and methods described herein. The processor 1802 can be a variety of various processors including dual microprocessor and other multi-processor architectures.

The memory 1804 can include volatile memory and/or non-volatile memory. The non-volatile memory can include, but is not limited to, ROM, PROM, EPROM, electrically erasable programmable read only memory (EEPROM), and the like. Volatile memory can include, for example, RAM, synchronous RAM (SRAM), dynamic RAM (DRAM), synchronous DRAM (SDRAM), double data rate SDRAM (DDR SDRAM), and direct RAM bus RAM (DRRAM). The disk 1806 can include, but is not limited to, devices like a magnetic disk drive, a floppy disk drive, a tape drive, a Zip drive, a flash memory card, and/or a memory stick. Furthermore, the disk 1806 can include optical drives like, compact disk ROM (CD-ROM), a CD recordable drive (CD-R drive), a CD rewriteable drive (CD-RW drive) and/or a digital versatile ROM drive (DVD ROM). The memory 1804 can store processes 1814 and/or data 1816, for example. The disk 1806 and/or memory 1804 can store an operating system that controls and allocates resources of the computer 1800.

The bus 1808 can be a single internal bus interconnect architecture and/or other bus architectures. The bus 1808 can be of a variety of types including, but not limited to, a memory bus or memory controller, a peripheral bus or external bus, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computer 1800 interacts with input/output devices 1818 via input/output ports 1810. Input/output devices 1818 can include, but are not limited to, a keyboard, a microphone, a pointing and selection device, cameras, video cards, displays, and the like. The input/output ports 1810 can include but are not limited to, serial ports, parallel ports, and USB ports.

The computer 1800 can operate in a network environment and thus is connected to a network 1820 by a network interface 1812. Through the network 1820, the computer 1800 may be logically connected to a remote computer 1822. The network 1820 includes, but is not limited to, local area networks (LAN), wide area networks (WAN), and other networks. The network interface 1812 can connect to local area network technologies including, but not limited to, fiber distributed data interface (FDDI), copper distributed data interface (CDDI), ethernet/IEEE 802.3, token ring/IEEE 802.5, and the like. Similarly, the network interface 1812 can connect to wide area network technologies including, but not limited to, point to point links, and circuit switching networks like integrated services digital networks (ISDN), packet switching networks, and digital subscriber lines (DSL).

The systems, methods, and objects described herein may be stored, for example, on a computer readable media. Media can include, but are not limited to, an ASIC, a CD, a DVD, a RAM, a ROM, a PROM, a disk, a carrier wave, a memory stick, and the like. Thus, an example computer readable medium can store computer executable instructions for a method for screening tissue. The method can include directing an ultrasonic wave at a tissue to be screened, receiving a second ultrasonic wave produced by the first ultrasonic wave interacting with the tissue to be screened, and determining whether an area of the tissue to be screened should be tagged. The determining can include analyzing a parameter associated with the second ultrasonic waves in the context of a tissue mechanical properties model. In one example, the method can also include associating a nanoparticle contrast agent with the tissue to be screened.

Furthermore, a computer readable medium may store a data structure associated with a biomechanical response model and/or a reflection coefficient model. An example model may include, a first field that stores information associated with tissue reflection properties. For example, the tissue reflection properties may include, but are not limited to, reflection coefficients, or reflection spectra. The model may also include a second field that stores information associated with tissue health properties. For example, the tissue health properties may include, but are not limited to, status, degree of invasion, and the like. The model may also include a third field that stores correlation information associated with correlating the tissue reflection properties of the first field and the tissue health properties of the second field. Thus, the model can facilitate retrieving a tissue health property given a tissue reflection property, and/or can facilitate retrieving a tissue reflection property given a tissue health property.

Similarly, an example computer readable medium can store computer executable components of a tissue screening system. The tissue screening system can include, for example, an ultrasonic wave producer that produces a first ultrasonic wave that is directed at a tissue to be screened, an ultrasonic wave receiver that receives one or more second ultrasonic waves, where the second ultrasonic waves are produced by the first ultrasonic wave interacting with the tissue to be screened, and an analyzer operably connected to one or more of the ultrasonic wave producer and the ultrasonic wave receiver, where the analyzer differentiates tissue regions in the tissue to be screened based, at least in part, on analyzing one or more relationships between the first ultrasonic wave and the second ultrasonic wave. In another example, the system may include a tissue mechanical properties model in data communication with the analyzer.

Figure 18:
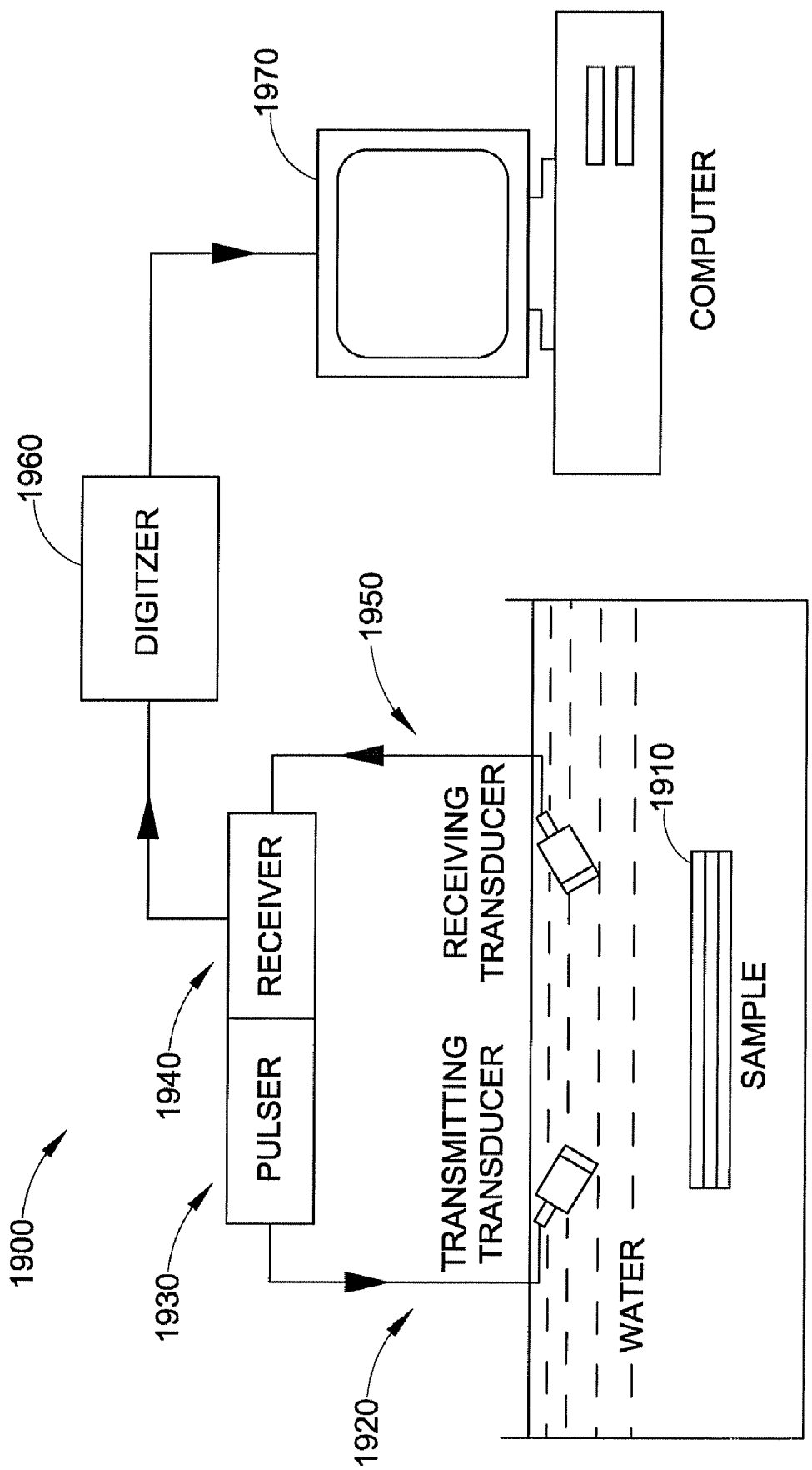
FIG. 18 illustrates an example tissue screening system.

Computer readable media may be employed in a system like that illustrated in FIG. 18. The elements of an example basic ultrasound nondestructive evaluation system 1900 are shown in FIG. 18. Such a nondestructive evaluation system 1900 could be employed, for example, in developing a nanomechanical bioresponse model, a reflection coefficient model, and/or in an automated slide reader. The energy-provider of the system 1900 is the pulser section 1930 of a pulser-receiver. The pulser 1930 may generate short (e.g., 0.1 µsec), repetitive (e.g., 1 msec apart) electrical pulses. The electrical pulses may be, for example, on the order of several hundred volts, and they drive a transducer 1920 (e.g., piezoelectric material) to produce mechanical vibrations, which then transmit as a beam of ultrasound in media.

If the ultrasound beam hits a material discontinuity while propagating in a medium, a portion of the energy will be reflected/scattered and transmitted along another direction of wave propagation. The reflected/scattered or transmitted signals can be detected by a receiving transducer 1950, which transforms mechanical pulses into electrical pulses. The receiver transducer 1950 can transform mechanical energy into electrical energy, which is then processed by receiver 1940.

The electrical energy transferred from ultrasound vibrations is usually small, for example, on the order of 0.001 volt. The electrical energy can be amplified, for example, to the order of 1 volt through an amplifier. The waves of the electrical pulses can be displayed as a voltage versus time trace on an oscilloscope or the screen of a computer 1970.

Further processing and quantitative evaluation on the received signals is facilitated by capturing and storing the received signals. This is achieved through a digitizer 1960 (e.g., digital oscilloscope, external digitizer with high sampling rate (e.g., above 100 MHz)) to preserve details in the signals. Once in the digital form, the signals can be readily stored in the computer 1970 for analysis.

Figure 19:
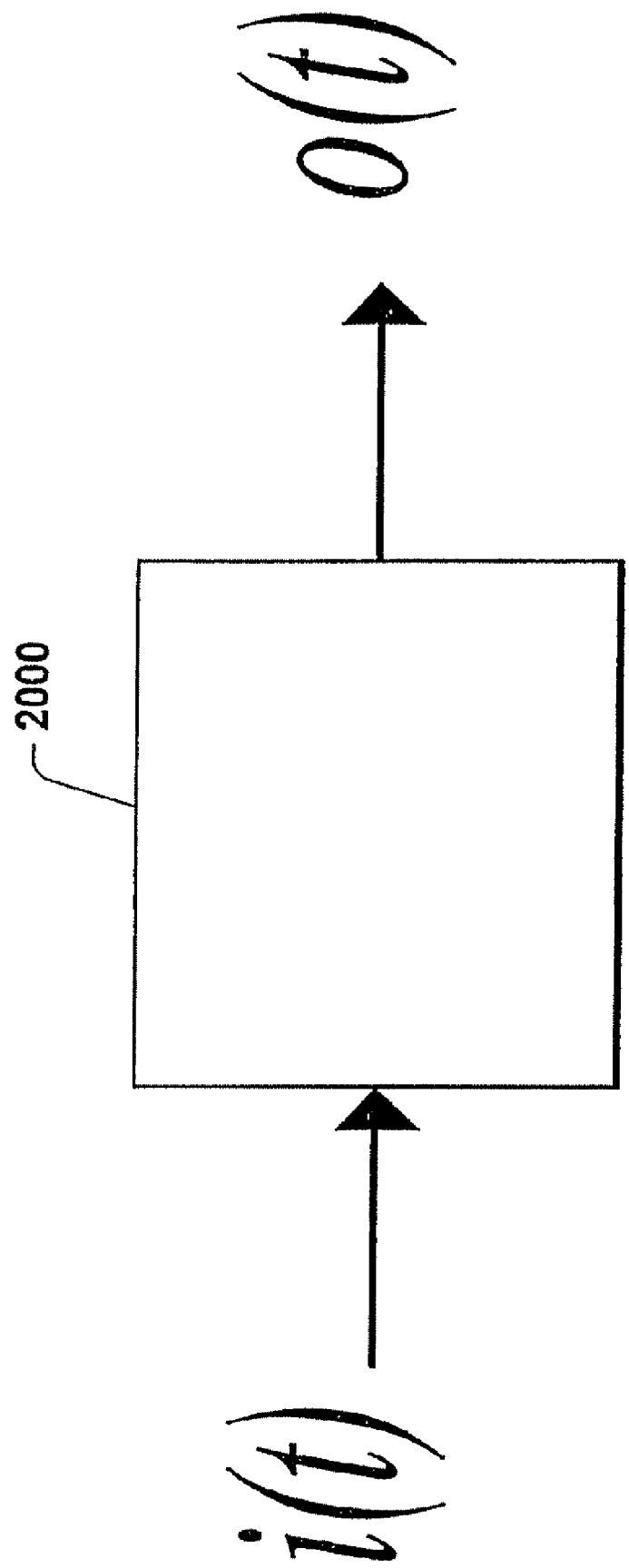
FIG. 19 illustrates an input-output system.

Systems like those described in FIG. 18 can be generically classified as input-output systems. Thus, FIG. 19 illustrates an example of a generic input-output system 2000, where the system 2000 takes input i(t) to produce an output o(t). Both i(t) and o(t) are functions of time t. One example ultrasonic measurement system for biological tissue samples may have components that are themselves complex electromechanical systems. A simplification can be achieved by treating the components, and therefore the overall system, as Linear Time-Shift Invariant (LTI) systems, where $$o(t)=L[i(t)]$$

The linearity of the system depends on:

$$o(t)=L[c_1 i_1(t)+c_2 i_2(t)]=c_1 L[i_1(t)]+c_2 L[i_2(t)]$$

where $i_1$ and $i_2$ are two arbitrary inputs and $c_1$ and $c_2$ are two arbitrary constants.

The time-shift invariant property of LTI system depends on:

$$o(t-t_0)=L[i(t-t_0)]$$

which means that a delay in the input signal produces a corresponding delay in the output.

Figure 20:
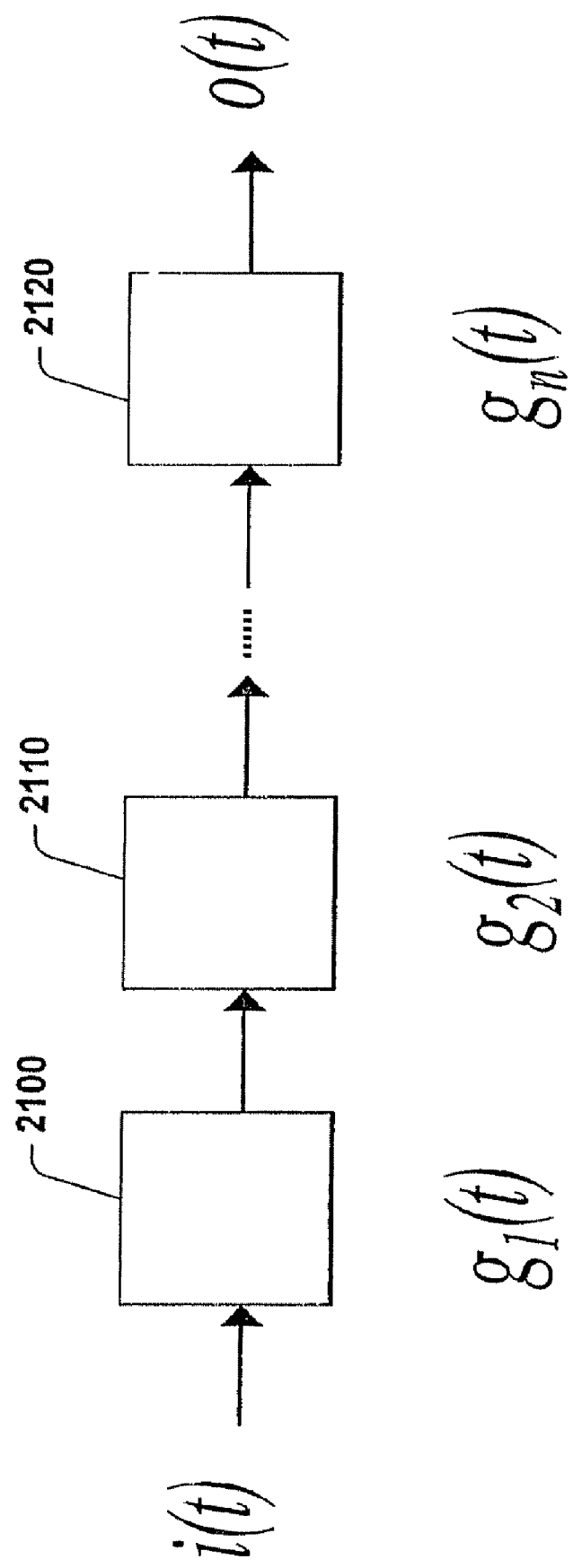
FIG. 20 illustrates a series of input-output systems.

For a system comprised of multiple LTI systems, (e.g., input-output systems 2100, 2110, 2120), like the system illustrated in FIG. 20, the overall response in time-domain is determined by the convolution of the impulse response of each component:

$$o(t)=g_1(t)*g_2(t)* \ldots *g_n(t)*i(t)$$

where $g_k(t)$ is the impulse response of the kth component.

Convolution in time-domain is equivalent to product in frequency domain. A useful technique in analyzing such a system is Fourier Transformation that describes the responses in terms of the decomposition of a pulse (time domain signal) into a distribution of sinusoids with different magnitudes at different frequencies. Through Fourier transformation, the response of the overall system can be obtained from products of the component responses rather than from complicated multiple convolution integrals in time domain.

$$O(\omega)=G_1(\omega)G_2(\omega) \ldots G_n(\omega)I(\omega)$$

One example input-output system may be an automated pathology slide reader. The slider reader may include a slide holder for holding a slide on which tissue is located, and an ultrasound wave generator for producing incident ultrasonic waves that are directed at the slide at an incident angle. The slide may include, for example, a tissue sample sandwiched between two plates of substrates (e.g., glass). In one example, the slide may be immersed in a fluid (e.g., water) when it is subjected to ultrasonic wave analysis. The system may also include an ultrasound wave receiver for receiving a reflected ultrasonic wave produced by the incident wave interacting with the tissue on the slide, where the reflected ultrasonic wave is reflected from the slide at a reflection angle. The system may also include a comparison computer component for comparing data associated with items including, but not limited to, the incident angle, the reflected angle, the reflection spectrum, the incident wave, and the reflected wave. The comparison computer component, and/or other computer components may also determine one or more tissue properties based, at least in part, on the analyzed data in the context of a biomechanical response model.

In one example, the slide reader may be configured so that the incident angle is an angle between the two mode conversion angles of the first layers and the fluid in which the slide is imnersed. In another example, the slide reader may be configured so that the incident angle is between 15 and 20 degrees.

The systems and methods described herein can be employed to build models that facilitate characterizing tissue responses to ultrasonic waves. One method for building a model that characterizes tissue response to ultrasonic waves includes acquiring a set of known normal tissue samples. For example, healthy tissue can be collected from a patient or set of patients. The method then includes analyzing the set of normal tissue samples employing ultrasonic waves and a nanomechanical representation of the normal tissue samples to produce a first analysis data. The first analysis data can include, for example, reflection coefficients, reflection spectra, elasticity information, tissue micro-architecture information, and so on. The method then includes acquiring a set of known malignant tissue samples and analyzing the set of known malignant tissue samples employing ultrasonic waves and a nanomechanical representation of the malignant tissue samples to produce a second analysis data. The second analysis data can include, for example, reflection coefficients, reflection spectra, elasticity information, tissue micro-architecture information, and the like.

The method also includes characterizing tissue based, at least in part, on the first analysis data, the second analysis data, and the nanomechanical representation of tissue. The characterization can produce a characterization data that can be stored in a computer data store and/or processed by a computer component. The method also includes building a model that stores data including, but not limited to, the first analysis data, the second analysis data, and the characterization data.

What has been described above includes several examples. It is, of course, not possible to describe every conceivable combination of components or methodologies for purposes of describing the methods, systems, computer readable media, and so on employed in screening tissue. However, one of ordinary skill in the art may recognize that further combinations and permutations are possible. Accordingly, this application is intended to embrace alterations, modifications, and variations that fall within the scope of the appended claims. Furthermore, to the extent that the term "includes" is employed in the detailed description or the claims, it is intended to be inclusive in a manner similar to the term "comprising" as that term is interpreted when employed as a transitional word in a claim.

What is claimed is:

1. A tissue screening system, comprising:
   an ultrasonic wave producer that produces a first ultrasonic wave directed at a tissue to be screened;
   an ultrasonic wave receiver receiving a second ultrasonic wave produced as a function of the first ultrasonic wave interacting with the tissue;
   an analyzer operably connected to at least one of the ultrasonic wave producer and the ultrasonic wave receiver, the analyzer identifying whether the tissue is diseased tissue based on microstructural and micromechanical properties of the tissue, as compared to microstructural and micromechanical properties of normal tissue, from analysis of the second ultrasonic wave; and
   a tissue mechanical properties model, based on nanomechanics, in data communication with the analyzer, the tissue mechanical properties model processing information associated with the microstructural and micromechanical properties of normal and abnormal tissues from the second ultrasonic wave.

2. The system of claim 1, wherein the tissue mechanical properties model stores information concerning at least one of tissue reflection, tissue transmission, tissue elasticity, tissue particle size, tissue micro-architecture, and tissue micromoduli.

3. The system of claim 1, wherein the analyzer analyzes the second ultrasonic wave to characterize the mechanical reaction of the first ultrasonic wave with the tissue to facilitate identifying the tissue mechanical property which in turn facilitates determining if the tissue is one of healthy and diseased.

4. The system of claim 1, wherein the tissue mechanical properties model is based on one of a linear and non-linear viscoelastic model.

5. The system of claim 1, wherein the tissue to be screened is one of an external tissue surface and an internal tissue surface.

6. The system of claim 1, wherein the second ultrasonic wave includes a reflected wave.

7. The system of claim 1, wherein the second ultrasonic wave includes a transmitted wave.

8. The system of claim 1, wherein the analyzer analyzes a reflection spectrum.

9. The system of claim 1, wherein the tissue is treated with a nanoparticle contrast agent before the first ultrasonic wave is directed at the tissue.

10. The system of claim 1, wherein the ultrasonic wave producer and the ultrasonic wave receiver are both located in a portable device that is passed over the tissue.

11. The system of claim 1, wherein the ultrasonic wave producer is one of a transducer and a transducer array.

12. The system of claim 1, wherein the ultrasonic wave receiver is one of a transducer and a transducer array.

13. The system of claim 1, wherein the first ultrasonic wave is in the range of about 2.5 to about 12.5 MHz, with a center frequency of about 7.5 MHz.

14. The system of claim 1, wherein the first ultrasonic wave is in a range with a lower bound between about 2 and about 7 MHz and an upper bound between about 8 and about 13 MHz.

15. A non-transitory computer readable medium storing computer executable components of the system of claim 1.

16. The system of claim 1, wherein the analyzer identifies changes in at least one of micromoduli, internodal distance, and particle size microstructures of the tissue.

17. A method for screening tissue, comprising:
   directing an ultrasonic wave at a tissue to be screened;
   receiving a second ultrasonic wave produced as a function of the first ultrasonic wave interacting with the tissue;
   identifying, based on wave propagation mechanics, a parameter of the second ultrasonic wave associated with microstructural and micromechanical properties of the tissue;
   analyzing the parameter associated with the microstructural and the micromechanical properties of the tissue;

comparing the microstructural and the micromechanical properties of the tissue with microstructural and micromechanical properties of normal tissue based on a tissue mechanical properties model, based on nanomechanics, that processes information associated with the microstructural and micromechanical properties of normal and abnormal tissues from the second ultrasonic wave; and determining whether the tissue should be tagged as diseased tissue as a function of the parameter.

18. The method of claim 17, wherein the first ultrasonic wave has a frequency in the range of about 3 to about 13 MHz.

19. The method of claim 17, wherein the second ultrasonic wave comprises at least one of reflected waves and transmitted waves.

20. The method of claim 17, further comprising:
before directing the ultrasonic wave at the tissue, associating a nanoparticle contrast agent with the tissue.

21. The method of claim 17, wherein identifying the parameter comprises:
analyzing at least one of tissue reflection, tissue transmission, tissue elasticity, tissue particle size, tissue micromoduli, tissue micro-architecture, and tissue mechanical response properties.

22. A computer readable medium storing computer executable instructions operable to perform computer executable portions of the method of claim 17.

23. A tissue screening system, comprising:
means for generating a first ultrasonic wave;
means for directing the first ultrasonic wave at a tissue sample to be screened;
means for collecting a second ultrasonic wave produced from a mechanical interaction of the first ultrasonic wave and the tissue sample to be screened;
means for modeling one or more modeled mechanical properties of tissue, based on nanomechanics, into modeled microstructural and micromechanical properties of normal tissue based on wave propagation mechanics;
means for correlating the at least one of the microstructural and the micromechanical properties with one or more mechanical interactions between a tissue sample and an ultrasonic wave; and
means for identifying diseased regions of the tissue sample based on a comparison of the at least one of the microstructural and the micromechanical properties of the tissue with the modeled microstructural and the micromechanical properties of normal tissue.

* * * * *